(12) United States Patent
LoPresti et al.

(10) Patent No.: US 12,070,530 B2
(45) Date of Patent: Aug. 27, 2024

(54) DECELLULARIZATION AND FUNCTIONALIZATION OF EXTRACELLULAR MATRIX BIOMATERIALS

(71) Applicant: University of Pittsburgh—Of the Commonwealth System of Higher Education, Pittsburgh, PA (US)

(72) Inventors: Samuel LoPresti, Pittsburgh, PA (US); Bryan N. Brown, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 607 days.

(21) Appl. No.: 16/761,371

(22) PCT Filed: Nov. 9, 2018

(86) PCT No.: PCT/US2018/060051
§ 371 (c)(1),
(2) Date: May 4, 2020

(87) PCT Pub. No.: WO2019/094734
PCT Pub. Date: May 16, 2019

(65) Prior Publication Data
US 2020/0360564 A1  Nov. 19, 2020

Related U.S. Application Data

(60) Provisional application No. 62/583,846, filed on Nov. 9, 2017.

(51) Int. Cl.
*A61L 27/36* (2006.01)

(52) U.S. Cl.
CPC ....... *A61L 27/3687* (2013.01); *A61L 27/3633* (2013.01); *A61L 27/3691* (2013.01); *A61L 2430/34* (2013.01)

(58) Field of Classification Search
CPC ............. A61L 27/3687; A61L 27/3633; A61L 27/3691; A61L 2430/34; A61F 2/0063
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,216,115 A | 6/1993 | Kohn et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,711,969 A | 1/1998 | Patel et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,371,992 B1 | 4/2002 | Tanagho et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak et al. |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 8,361,503 B2 | 1/2013 | Badylak et al. |
| 8,470,520 B2 | 6/2013 | Ott et al. |
| 8,535,719 B2 | 9/2013 | Badylak et al. |
| 8,557,277 B2 * | 10/2013 | Virkler ................ A61L 27/3633 424/443 |
| 10,092,676 B2 | 10/2018 | Amoroso et al. |
| 2003/0228692 A1 | 12/2003 | Goldstein et al. |
| 2008/0260831 A1 | 10/2008 | Badylak et al. |
| 2010/0189759 A1 | 7/2010 | Padmini et al. |
| 2011/0082545 A1 | 4/2011 | Freund |

FOREIGN PATENT DOCUMENTS

| | | |
|---|---|---|
| CA | 2125037 A1 | 5/1993 |
| WO | 9843621 A1 | 10/1998 |
| WO | 2016090373 A1 | 6/2016 |
| WO | 2017123883 A1 | 7/2017 |
| WO | 2017151862 A1 | 9/2017 |

(Continued)

OTHER PUBLICATIONS

Krausz et al. Nitric oxide as a surgical adjuvant. Future Sci. OA. 2015;1(1):1-11.*
Angelo. Copper + Nitric Acid. www.angelo.edu. 2003;1-2.*
Ray et al. A New Method of Preparing Nitric Oxide. Journal of the American Chemical Society. 1956;78(23):5993.*
Dhandayuthapani et al. Polymeric Scaffolds in Tissue Engineering Application: A Review. International Journal of Polymer Science. 2011;2011:1-20.*
Attri et al. Generation mechanism of hydroxyl radical species and its lifetime prediction during the plasma-initiated ultraviolet (UV) photolysis. Scientific Reports. 2015;5:9332.*
Brown et al., "Macrophage Phenotype as a Predictive of Constructive Remodeling following the Implantation of Biologically Derived Surgical Mesh Materials", Acta Biomater, Mar. 2012, pp. 1-23, vol. 8(3), National Institute of Health.

(Continued)

*Primary Examiner* — Lynn Y Fan
(74) *Attorney, Agent, or Firm* — The Webb Law Firm

(57) ABSTRACT

Provided is a method of preparing an ECM material and the product of the method. The method comprises processing the ECM material with a reactive oxygen species or a reactive nitrogen species. Also provided are methods of use of the product.

13 Claims, 17 Drawing Sheets

(56) References Cited

FOREIGN PATENT DOCUMENTS

WO    2018175234 A1    9/2018

OTHER PUBLICATIONS

Brown et al., "Expanded applications, shifting paradigms and an improved understanding of host-biomaterial interactions", Acta Biomaterialia, 2013, pp. 4948-4955, vol. 9, SciVerse ScienceDirect.

Chumakov et al., "Electro-Fenton-like reactions of transition metal ions with electrogenerated hydrogen peroxide", AIP Conference Proceedings, 2016, pp. 040004-1-040004-6, vol. 1772, AIP Publishing.

Elgawish et al., "Involvement of Hydrogen Peroxide in Collagen Cross-linking by High Glucose in Vitro and in Vivo", The Journal of Biological Chemistry, May 31, 1996, pp. 12964-12971, vol. 270 No. 22, The American Society for Biochemistry and Molecular Biology, Inc.

Fang, "Antimicrobial Reactive Oxygen and Nitrogen Species: Concepts and Controversies", www.nature.com/reviews/micro, Oct. 2004, pp. 1-13, vol. 802, Departments of Laboratory Medicine and Microbiology, University of Washington School of Medicine, Seattle, WA.

Fields et al., "Extracellular matrix nitration alters growth factor release and activates bioactive complement in human retinal pigment epithelial cells", Plos One, May 15, 2017, pp. 1-18, https://doi.org/10.1371/journal.pone.0177763.

Foster et al., "Protein S-nitrosylation in health and disease: a current perspective", National Institute of Health, Sep. 2009, pp. 1-26, vol. 15(9), Elsevier Ltd.

Gao et al., "The ECM-Cell Interaction of Cartilage Extracellular Matrix on Chondrocytes", BioMed Research International, 2014, pp. 1-8, vol. 2014, Article ID 648459, Hindawi Publishing Corporation.

Grainger, "All charged up about implanted biomaterials", Nature Biotechnology, Jun. 2013, pp. 507-509, vol. 31, No. 6, Nature America, Inc.

Guyette et al., "Perfusion decellularization of whole organs", May 29, 2014, pp. 1451-1468, vol. 9 No. 6, Nature Protocols.

Hawkins et al., "Oxidative damage to collagen and related substrates by metal ion/hydrogen peroxide systems: random attack or site-specific damage?", Biochimica et Biophysics Acta, 1997, pp. 84-96, vol. 1360, Elsevier.

Huleihel et al. "Matrix-Bound Nanovesicles Recapitulate Extracellular Matrix Effects on Macrophage Phenotype", 2017, pp. 1283-1294, vol. 23, Nos. 21 and 22, Mary Ann Liebert, Inc.

Martinez-Ruiz et al., "S-nitrolysation a potential new paradigm in signal transduction", Cardiovascular Research, 2004, pp. 43-52, vol. 62, Elsevier.

Meixsell-Arnold et al., "Cost vs Healing Rates of Two Advanced Wound Therapies: A Pilot Study", Wounds, 2014, pp. E48-E52, vol. 26(6), www.woundsresearch.com.

Paik et al., "The Nitrite/Collagen Reaction: Non-Enzymatic Nitration as a Model System for Age-Related Damage", Connective Tissue Research, 2001, pp. 111-122, vol. 42(2), Francis and Taylor, Inc.

Pignatelli et al., "Hydrogen Peroxide Is Involved in Collagen-Induced Platelet Activation", Blood, Jan. 15, 1998, pp. 484-490, vol. 91, No. 2, The American Society of Hematology.

Shah et al., "Oxidative stress and its biomarkers in systemic lupus erythematosus", Journal of Biomedical Science, Mar. 2014, pp. 1-13, vol. 21:23, BioMed Central.

Stankus et al., "Hybrid nanofibrous scaffolds from electrospinning of a synthetic biodegradable elastomer and urinary bladder matrix", J Biomater Sci Polym Ed., 2008, pp. 1-21, vol. 19(5), National Institute of Health.

Sun et al., "Protein S-Nitrolysation and Cardioprotection", Circ Res., Feb. 5, 2010, pp. 285-296, vol. 106(2), National Institute of Health.

Wang et al., "Hydrogen peroxide-mediated oxidative stress and collagen synthesis in cardiac fibroblasts: Blockade by tanshinone IIA", Journal of Ethnopharmacology, 2013, pp. 152-161, vol. 145, SciVerse Science Direct.

Wang et al. "Quantitative Analysis of Reactive Oxygen Species Photogenerated on Metal Oxide Nanoparticles and Their Bacteria Toxicity: The Role of Superoxide Radicals", Environmental Science & Technology, 2017, pp. 10137-10145, vol. 51, American Chemical Society, ACS Publications.

\* cited by examiner

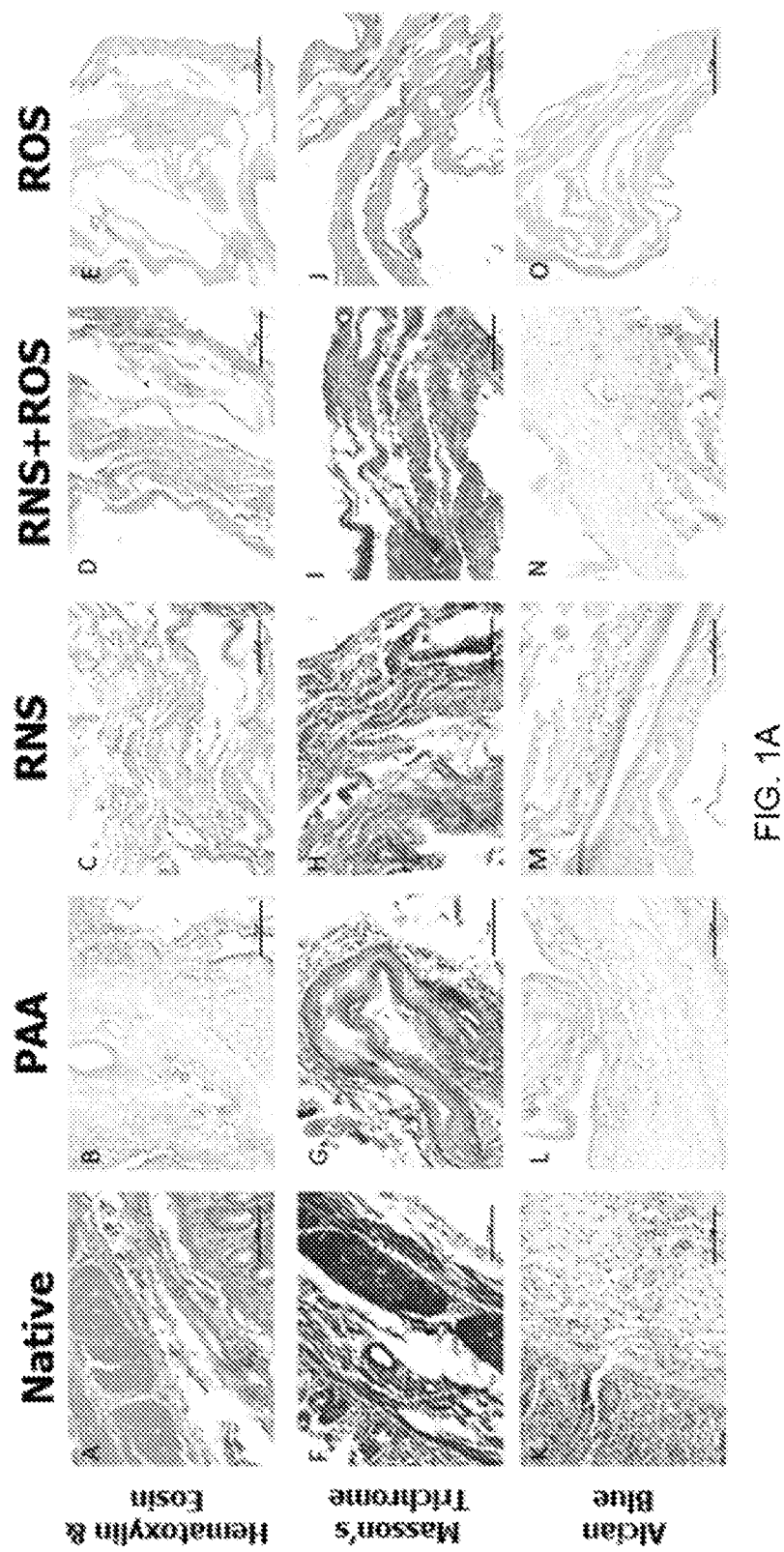

DECELLULARIZATION AND FUNCTIONALIZATION OF EXTRACELLULAR MATRIX BIOMATERIALS

CROSS REFERENCE TO RELATED APPLICATIONS

This application claims the benefit of U.S. Provisional Patent Application No. 62/583,846, filed Nov. 9, 2017, which is incorporated herein by reference in its entirety.

STATEMENT REGARDING FEDERAL FUNDING

This invention was made with government support under Grant Nos. AG043606 and HD043441, awarded by the National Institutes of Health. The government has certain rights in the invention.

Extracellular matrix biomaterials have been used clinically and pre-clinically in a wide variety of applications, including hernia repair, breast reconstruction, skin grafts and wound healing. Typically, extracellular matrix materials are prepared through the decellularization of mammalian tissues using detergents, enzymes and/or oxidants. When decellularized and prepared properly, extracellular matrix (ECM) biomaterials have been shown to promote constructive remodeling, defined as the formation of new site-appropriate host tissue. This positive outcome has been correlated with a shift during the acute immune response from a pro- (M1) to anti-inflammatory (M2) phenotype (macrophage polarization).

It is therefore desirable to provide ECM biomaterials having increased ability to promote constructive remodeling, e.g. by increasing the anti-inflammatory (M2) phenotype

SUMMARY

In one aspect, provided herein is a method of preparing an extracellular matrix (ECM) product. The method comprises contacting tissue or an ECM material with a reactive oxygen species (ROS) or a reactive nitrogen species (RNS) to produce an ECM product having nitroxidative or oxidative modifications. In another aspect, a product of the method of preparing an extracellular matrix (ECM) product is provided. In another aspect, a method of treating a wound, injury, or defect in a patient is provided. The method comprises administering to the patient at or about the site of the wound, injury, or defect, an amount of an ECM product prepared by the method of preparing an extracellular matrix (ECM) product effective to treat a wound or defect in a patient.

BRIEF DESCRIPTION OF THE DRAWINGS

FIGS. 1A and 1B (originals in color): Histologic assessment of decellularized extracellular matrix biomaterials. Hematoxylin & eosin (FIG. 1A, panels A-E (FIG. 1A (A-E)), Masson's trichrome (FIG. 1A (F-J)) and Alcian blue (FIG. 1A (K-O)) staining of histologic sections. Immunohistochemical staining for cysteine sulfonate (FIG. 1B (P-T)), S-nitro-cysteine (FIG. 1B (U-Y)), and 3-nitro-tyrosine (FIG. 1B (Z-AD)). All images at 10× (Scale bar=100 μm).

FIG. 4A is in color. Quantification of cellularity (FIG. 4B), collagen staining (FIG. 4C), glycosaminoglycan staining (FIG. 4D) and percent centralized muscle fiber nuclei (FIG. 4D). Scale bar=100 μm) Results presented as mean ±S.D. (* represents $p<0.05$,  $p<0.01$, * $p<0.001$, **** $p<0.0001$).

FIG. 5A is in color. Cell Profiler quantification of immunofluorescent staining for F4/80 (FIG. 5B), iNOS (FIG. 5C), arginase-1 (FIG. 5D) and heme oxygenase-1 (FIG. 5E). Scale bars=100 μm. Results presented as mean ±S.D. (* represents $p<0.05$, $p<0.01$, * $p<0.001$, **** $p<0.0001$).

DETAILED DESCRIPTION

Figure 1B:
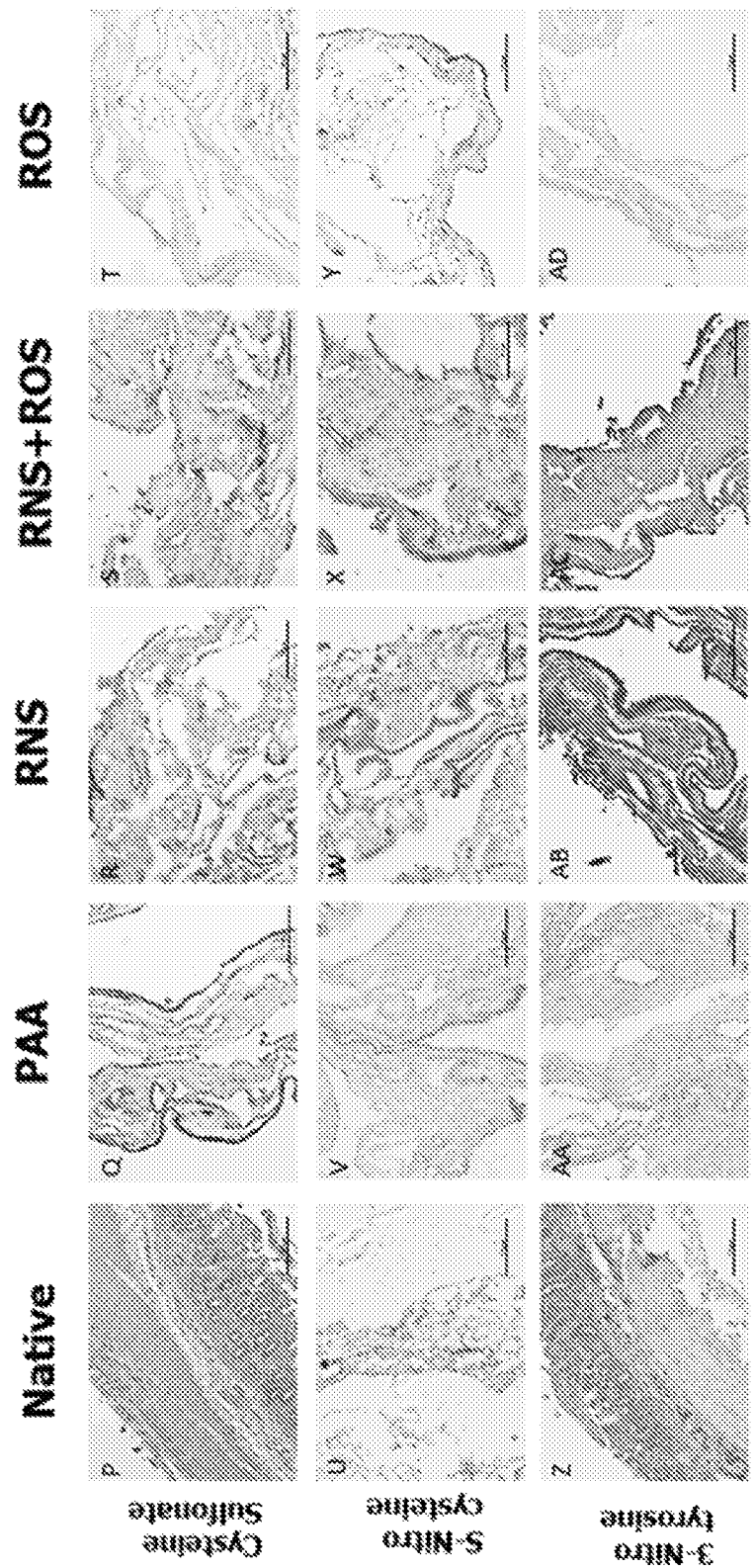

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "right", "left", "top", "bottom", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Figures are not drawn to scale, but are drawn in a manner to best depict the relationship between the various elements of the device drawn in the figure. Hence, specific dimensions and other physical characteristics related to the embodiments disclosed herein are not to be considered as limiting.

As used herein, the terms "comprising," "comprise" or "comprised," and variations thereof, are meant to be open ended. The terms "a" and "an" are intended to refer to one or more.

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a tricuspid or mitral valve.

As used herein, the term "patient" or "subject" refers to members of the animal kingdom including but not limited to human beings and "mammal" refers to all mammals, including, but not limited to human beings.

A polymer composition is "biocompatible" in that the polymer and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers and refers to both refers to both synthetic polymeric components and biological polymeric compositions. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning. Homopolymers contain one type of building block, or monomer, whereas copolymers contain more than one type of monomer. The term "(co)polymer" and like terms refer to either homopolymers or copolymers. "Biological polymer(s)" are polymers that can be obtained from biological sources, such as, without limitation, mammalian or vertebrate tissue, such as collagen, fibrin, or elastin. Biological polymers can be chemically modified by additional processing steps.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g., terminal groups, that are modified during polymerization are changed, removed, and/or relocated, and certain bonds may be added, removed, and/or modified. A monomer may be a "macromer", an oligomer or polymer that is the combination product of two or more smaller residues, and is employed as a monomer in preparation of a larger polymer. An incorporated monomer is referred to as a "residue" of that monomer.

A "moiety" is a portion of a molecule, compound or composition, and includes a residue or group of residues within a larger polymer.

A polymer is said to comprise a specific type of linkage if that linkage is present in the polymer, thus, a polyester comprises a plurality of ester linkages, a polyurethane comprises a plurality of urethane (e.g., carbamate) linkages, and a poly(ester urethane) urea comprises ester, urethane, and urea linkages. Unless otherwise specified, molecular weight for polymer compositions refers to weight average molecular weight (Mw). Composition of a copolymer may be expressed in terms of a ratio, typically a molar ratio, of incorporated monomers or as a feed ratio of monomers prior to polymerization. In the case of feed ratios, the relative amount of each monomer incorporated into the copolymer is influenced by reaction kinetics, and the nature of the chemical reaction(s) employed to join the monomers.

As described herein, a "fiber" is an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic. A "cell growth scaffold" is a matrix, e.g. a porous structure, upon which cells can be cultured in vitro, ex vivo, or in vivo, e.g., in any suitable cell culturing device, tissue culturing device, or organ culturing device, such as, for example and without limitation: a flask, a tissue culture dish, a multi-well culture dish, or a fluidic cell, tissue or organ culturing system, or bioreactor, or implanted in vivo, such as in a mammal or a human. A cell growth scaffold may be considered biocompatible, but does not necessarily require that the cells grown thereon or therein divide, differentiate, multiply, or otherwise increase in number, but cell growth thereon or therein, cell division, cell differentiation, cell multiplication, or any increase in cell number, and/or formation of specific tissue structures may be preferred in instances.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. Bioerodible polymers degrade in vivo over a time period. "Non-bioerodible" polymers do not degrade to any significant extent in vivo over a time period of at least two years, for instance, they do not degrade substantially in vivo in five or ten years, and include polyethylene terephthalate (PET, including DACRON®) and PTFE (polytetrafluoroethylene, including expanded PTFE (ePTFE, W. L. Gore), and TEFLON®), which are often used in implantable medical devices.

As used herein, the terms "extracellular matrix" and "ECM" refer to a natural scaffolding for cell growth. ECM is a complex mixture of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue. Activity of the biomolecules within the ECM can be affected or removed chemically or mechanically, for example, by cross-linking and/or by dialyzing the material. In one aspect, the ECM materials described herein essentially have not been cross-linked and/or dialyzed, meaning that the ECM has not been subjected to a dialysis and/or a cross-linking process in anything but a trivial manner which does not substantially affect the functional characteristics, and, where relevant, gelation of the ECM material in its uses described herein.

As used herein, the term "derive" and any other word forms or cognates thereof, such as, without limitation, "derived" and "derives", refers to a component or components obtained from any stated source by any useful method. For example and without limitation, generically, an ECM-derived gel refers to a gel comprised of components of ECM obtained from any tissue by any number of methods known in the art for isolating ECM. In another example, mammalian tissue-derived ECM refers to ECM comprised of components of a particular mammalian tissue obtained from a mammal by any useful method.

Decellularized or devitalized ECM can be dried, either lyophilized (freeze-dried) or air dried. The ECM composition is optionally comminuted at some point, for example prior to acid protease digestion in preparation of an ECM gel, for example prior to or after drying. The comminuted ECM can also be further processed into a powdered form by methods, for example and without limitation, such as grinding or milling in a frozen or freeze-dried state. As used herein, the term "comminute" and any other word forms or cognates thereof, such as, without limitation, "comminution" and "comminuting", refers to the process of reducing larger particles, e.g., of dried ECM, into smaller particles, including, without limitation, by tearing, grinding, blending, shredding, slicing, milling, cutting, shredding, shearing, and pulverizing. ECM can be comminuted while in any form, including, but not limited to, hydrated forms, frozen, air-dried, lyophilized, powdered, or sheet-form.

An "ECM material" or "ECM product" is decellularized or devitalized tissue that is prepared from an extracellular matrix-containing tissue, and does not consist of a single, isolated and purified ECM component, such as a purified collagen preparation, as are commercially available. Any type of tissue-derived material can be used to produce the ECM materials in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain aspects, the ECM material is isolated from a vertebrate animal, for example and without limitation, from a mammal, including, but not limited to, human, monkey, pig, cow and sheep. The ECM material can be prepared from any organ or tissue, including without limitation, urinary bladder, intestine, liver, nerve, esophagus, adipose tissue, and dermis.

Decellularized tissue is tissue processed such that it is free of viable cells, or is substantially free of viable cells, and is an ECM product. Tissue may be, at least in part, decellularized by any useful process, for example by comminution, contact with a proteinase such as trypsin, contact with a detergent, such as an ionic, a zwitterionic, or a non-ionic detergent, contact with an emulsifier, exposure to osmotic shock, exposure to pressure variations, freezing and thawing, nuclease digestion, and/or contact with disinfecting agents, such as peracetic acid, among a large variety of processing steps used to decellularize tissue to produce an ECM product, e.g., as are broadly-known to those of ordinary skill. In the context of the present invention, in aspects, tissue is, at least in part, decellularized by contact with a reactive oxygen species, including without limitation, hydroxyl radical, superoxide, nitric oxide, thyl radical, peroxyl radical, lipid peroxyl radical, peroxynitrite, hypochloric acid, hydrogen peroxide, singlet oxygen, ozone and lipid peroxide, or a reactive nitrogen species, including without limitation, nitrous oxide, peroxynitrite, peroxynitrous acid, nitroxyl anion, nitryl chloride, nitrosyl cation, nitrogen dioxide, dinitrogen trioxide, nitrous acid and nitric acid. As part of the processing of tissue to produce an ECM material, tissue that is sufficiently thin or finely divided may be treated solely with the ROS or RNS agent to produce a useful ECM product, though the material would be washed and optionally dried after such treatment. In aspects, the ECM is considered decellularized when there is less than 50 ng DNA/mg ECM in the decellularized ECM, digest solution and/or resulting pre-gel solution. In other aspects, the ECM is considered decellularized when there is less than 750 nmol phospholipids/g ECM in the solution and/or resulting pre-gel solution. In one example, tissue is enzymatically-digested in Trypsin, washed, e.g., with saline or PBS, treated with a detergent, such as a non-ionic detergent, such as Triton X-100, washed, treated with an ROS and/or an RNS, washed, and lyophilized for use.

The ECM material can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. Traditionally, ECM material is disinfected by immersion in 0.1% (v/v) peracetic acid (σ), 4% (v/v) ethanol, and 96% (v/v) sterile water for 2 h. The ECM material is then washed twice for 15 min with PBS (pH=7.4) and twice for 15 min with deionized water. In one aspect, the ROS or RNS treatment as described herein effectively sterilizes the ECM material.

Commercially available ECM products can also be used in various aspects of the methods, devices and compositions described herein. In one aspect, the ECM product is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Indiana) and Graft-Patch™ (Organogenesis Inc.; Canton Massachusetts). In another embodiment, the ECM is derived from dermis. Commercially available preparations include, but are not limited to Pelvicol™ (crosslinked porcine dermal collagen, sold as Permacol™ in Europe; Bard Medical Division, Covington, Ga), Repliform™ (Microvasive; Boston, Massachusetts) and Alloderm™ (LifeCell; Branchburg, New Jersey). In another embodiment, the ECM material is derived from urinary bladder. Commercially available preparations include, but are not limited to UBM (Acell Corporation; Jessup, Maryland).

In various aspects, ECM material is decellularized, sterilized and/or dried by any useful method. ECM-derived material can then be used in any form in the methods and compositions described herein. In certain aspects, e.g., to facilitate spraying or electrospraying the ECM material, the ECM material may be either finely comminuted, e.g. into micro-scale-sized (from 1-999 microns) or nano-scale-sized (from 1-999 nanometers) particles, or is solubilized, for example in the form of a pre-gel or gel, as described below. In aspects, an ECM gel, and methods of making an ECM gel, are provided. The ECM gel is reverse gelling, or can be said to exhibit reverse thermal gelation, in that it forms a gel upon an increase in temperature. As the temperature rises above a certain temperature in a reverse gel, a hydrogel is formed. The general concept of reverse gelation of polymers and, e.g., its relation to lower critical solution temperature (LCST) are broadly known in the chemical arts. The ECM compositions described herein are prepared, for example, from decellularized or devitalized tissue that has been treated with a ROS or RNS as described herein. An ECM gel is prepared by digestion of the ECM material with an acid protease under acidic conditions, neutralization of the material to form a pre-gel, and then raising the temperature of the pre-gel above a gelation temperature, for example the LCST of the pre-gel, to cause the pre-gel to gel. As used herein, the term "gel" includes hydrogels. The transition temperature for acid-protease-digested from solution to gel is typically within the range of from 10° C. to 40° C. and any increments or ranges therebetween, for example from 20° C. to 35° C. For example, the pre-gel can be warmed to 37° C. to form a hydrogel.

In aspects, in order to prepare solubilized ECM, ECM material, for example comminuted ECM material, is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases include pepsin and trypsin and mixtures thereof.

As an example, the digest solution of ECM is kept at a constant stir for a certain amount of time at room temperature. In one aspect, the pH is maintained at less than pH 4.0 or at pH 2.0±0.3 during acid protease digestion of the decellularized tissue as described herein. The ECM digest can be used immediately or can be stored at 4° C. or frozen at, for example and without limitation, −20° C. or −80° C. In certain aspects, the ECM digest is snap frozen in liquid nitrogen. To form a "pre-gel" solution, the pH of the digest solution is raised to a pH between 6.8 and 7.8. The pH can be raised by adding one or more of a base or an isotonic buffered solution, for example and without limitation, NaOH or PBS at pH 7.4. The method optionally does not include a dialysis step prior to gelation, yielding a more-complete ECM-like matrix that typically gels at 37° C. more slowly than comparable collagen or dialyzed ECM preparations. The gel therefore retains more of the qualities of native ECM due to retention of many native soluble factors, such as, without limitation, cytokines. These factors contribute to chemoattraction of cells and proper rearrangement of tissue at the site of injury, rather than a fibrotic response that leads to unwanted scarring. In other embodiments, the ECM is dialyzed prior to gelation to remove certain soluble components.

As used herein, the term "isotonic buffered solution" refers to a solution that is buffered to a pH between 6.8 and 7.8, e.g., pH 7.4, and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH, or NaOH in PBS. This "pre-gel" solution can, at that point be incubated at a suitably warm temperature, for example and without limitation, at about 37° C. to gel.

In the method of preparing an ECM gel, the ECM may be partially or completely digested with an acid protease, such as pepsin. The digested ECM is then neutralized to a pH of 6.8-7.8, e.g., 7.2-7.6, or 7.4 and the neutralized and digested ECM material is gelled by incubation at a temperature at which the material gels, e.g., at a temperature above 20, 25, 30, or 35° C., such as at 37°. The degree of digestion can be determined by comparison on a gel, or by ascertaining the degree of degradation of hyaluronic acid, for example by Western blot (anti-hyaluronic acid antibodies are commercially-available from multiple sources) or chromatographic methods, as are broadly known. For example in a partial digestion, hyaluronic acid is digested less than 50%, 40%, 30%, 25%, 20% or 10%.

Therefore, according to one aspect of the invention, an ECM composition is provided comprising devitalized, acid-protease-digested tissue, having a pH of from 6.8 to 7.8. In one aspect, the devitalized, acid-protease-digested tissue is not dialyzed or chemically crosslinked-meaning at no stage during the processing of intact tissue to produce the devitalized, acid-protease-digested tissue has the material been dialyzed or cross-linked by addition of a chemical cross-linking agent, as is common in the production of certain devitalized ECM materials. The material is treated at some point, e.g., prior to or after acid protease digestion, with an ROS or RNS to modify the ECM material accordingly.

In aspects, the ECM material may produce a gel, and in another aspect, the digested, solubilized ECM material does not produce a gel, but is used in a liquid state.

The ECM gel or solubilized ECM material can be sprayed as a liquid or hydrogel in the methods provided herein. An ECM gel may have an LCST (Lower Critical Solution Temperature) above or below the temperature at which the solution is sprayed, and as such will have a gel transition at a temperature higher, equal to or lower than the temperature at which the ECM gel is sprayed. For example, if the hydrogel is sprayed at room temperature (that is approximately 20-25° C.) or less and the LCST of the ECM material is greater than the spraying temperature, but, e.g., less than 37° C., the material can be sprayed and will later gel on warming, for example on implantation or when placed in an warm environment, e.g. at 37° in an incubator. Thus, in one aspect, an ECM gel with an LCST between 20° C. and 37° C., for example and without limitation approximately 25° C., is provided herein. See, e.g. United States Patent Publication No. 20080260831, incorporated herein by reference for its technical disclosure. See also, Stankus et al., Hybrid nanofibrous scaffolds from electrospinning of a synthetic biodegradable elastomer and urinary bladder matrix, J Biomater. Sci. Polym. Ed. (2008) 19(5):635-652. In another aspect, solubilized ECM does not form a gel, but can be used in the same manner, e.g. sprayed or otherwise applied as a wound dressing for use in treatment of a wound, such as a chronic wound, such as a diabetic foot ulcer.

In another example, at least one therapeutic agent is added to the article described herein before it is implanted in the patient or otherwise administered to the patient. Generally, the therapeutic agents include any substance that can be coated on, embedded into, absorbed into, adsorbed to, chemically linked to with a labile or digestible bond, or otherwise attached to or incorporated onto or into the structure or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another example, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), Human Vascular Endothelial Growth Factor-165 ($hVEGF_{165}$), Vascular endothelial growth factor A (VEGF-A), Vascular endothelial growth factor B (VEGF-B), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts In certain aspects, the therapeutic agent is an antimicrobial agent or antibiotic, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin; nitro-fatty acids, such as nitro-oleic acid or nitro-conjugated linoleic acid. Other drugs that may promote wound healing and/or tissue regeneration may also be included.

Cells, such as a patient's cells, such as stem cells, e.g., mesenchymal stem cells or adipose-derived mesenchymal stem cells, may be applied to, mixed into, cultured on ex vivo, or otherwise grown on the ECM product described herein prior to implantation. Blood or blood fractions, such as, for example and without limitation, serum, plasma, or platelet-rich plasma, may be combined with the ECM material in any manner.

Oxidative reagents used in decellularization have an interesting correlation with macrophage phenotype, as reactive oxygen species (ROS) and reactive nitrogen species (RNS) are produced by macrophages during inflammation. A common oxidant used in extracellular matrix decellularization is peracetic acid, a stabilized form of hydrogen peroxide. Hydrogen peroxide itself is an important inflammatory mediator and damage signal which can modify proteins via cysteine oxidation and lipids via lipid peroxidation. The oxidative modification of extracellular matrix biomaterials by peracetic acid used during decellularization may be responsible, in part, for the beneficial host responses observed following implantation. In addition, peracetic acid serves as a sterilization step through protein denaturation, cell wall permeabilization, and sulfur oxidation in proteins and enzymes which can inactivate bacteria, viruses and spores.

According to aspects of the invention, tissue or ECM material is contacted with an ROS and/or an RNS to produce a modified ECM material as described herein. Tissue, or ECM material is contacted with an ROS or an RNS to produce the material. As shown herein, decellularization of extracellular matrix biomaterials with more potent RNS and ROS mediators further enhances the promotion of an anti-inflammatory phenotype. ROS have been shown to promote the polarization of macrophages to an anti-inflammatory phenotype. Nitric oxide signaling, which is important in angiogenesis and oxidative burst, also signals macrophages to polarize to an anti-inflammatory state via VASP signaling. Reactive nitrogen species themselves and modification of fatty acids has been shown to reduce pro-inflammatory macrophage phenotype. Reactive oxygen and nitrogen species have also been shown to induce an anti-oxidant oxidative stress pathway via the Nrf2 transcription factor which could be beneficial for the treatment of ischemic injuries. ROS or RNS decellularization methods pose a novel, potential alternative which can enhance or modify the beneficial effects of extracellular matrix biomaterials.

Therefore, provided herein are methods of producing ECM products, ECM products, and uses for the ECM products. Production methods for ECM products involve decellularization or devitalization of tissue, e.g., mammalian tissue. The method disclosed herein modifies tissue or ECM product by contact with a reactive oxygen species (ROS) or a reactive nitrogen species (RNS). ROS and RNS can be obtained in any useful form or prepared in any useful manner, so long as the reagents applied to the tissue are biocompatible or are removed, e.g., by washing, prior to use in a living organism or culture system. ROS or RNS can be supplied through use of a catalyst and/or chemical compound(s) that contain or produce ROS or RNS. For example, during processing of the tissue to produce the ECM product, a compound or combinations of compounds can be added at one point during processing, to expose the tissue or devitalized tissue to the ROS or RNS.

ECM material in any form, such as a sheet, a solid, a gel, or a liquid, may be combined with synthetic materials, such as gauzes or fibrous mats, e.g., in layers or absorbed into or adsorbed onto any suitable material or prosthetic, for example and without limitation, as described in U.S. Pat. Nos. 8,535,719 and 10,092,676, and International Patent Publication No. WO 2018/175234, each of which is incorporated herein by reference, and describing various forms of hybrid materials comprising a synthetic polymer composition combined with an ECM material. ECM material also includes nanovesicles derived from an ECM or nanovesicles, e.g., as described in International Patent Publication No. WO 2017/151862, which is incorporated herein by reference. A prosthetic, or implanted device may include a coating or covering of the material described herein.

Reactive oxygen species (ROS) are compounds or moieties that include chemically reactive chemical species containing oxygen, or are able to form chemically reactive chemical species containing oxygen under typical conditions. ROS includes radicals and non-radicals. Non-limiting examples of ROS include: hydroxide (OH.), Superoxide ($O_2^-$), nitric oxide (NO.), thiyl (RS.), forming $RSO_2$. in the presence of oxygen and copper or iron ions), peroxyl (ROO.), lipid peroxyl (LOO.), peroxynitrite ($ONOO^-$), hypochloric acid (HOCl), singlet oxygen ($^1O_2$), ozone ($O_3$), and lipid peroxide (LOOH).

Reactive nitrogen species (RNS) are compounds or moieties that include chemically reactive chemical species containing nitrogen, or are able to form chemically reactive chemical species containing nitrogen under typical conditions. RNS includes radicals and non-radicals. Non-limiting examples of RNS include: nitric oxide, peroxynitrite ($ONOO^-$), peroxynitrous acid (ONOOH), nitroxyl anion ($NO^-$), nitryl chloride ($NO_2Cl$), nitrosyl cation ($NO^+$), nitrogen dioxide ($NO_2$.), dinitrogen trioxide ($N_2O_3$), and nitrous acid ($HNO_2$).

In one aspect, treatment with the ROS or RNS is sufficient to decellularize and devitalize tissue, such as thin sheets or small tissue particles, e.g., finely comminuted tissue. One example of this is the preparation of ECM material from SIS, as described herein. In other aspects, additional treatments are needed aside from contacting the tissue or ECM product with the ROS or RNS. For example, prior to contacting the material with the ROS or RNS, the tissue is partially or fully prepared as an ECM product, and even can be treated with peracetic acid prior to treatment with the ROS or RNS. In one aspect, a commercially-available ECM product is treated with the ROS or RNS.

The ROS and RNS may be supplied or prepared in any manner compatible with the end use of the ECM product. In one aspect, the ROS or RNS is prepared separately and is then introduced into a solution containing the tissue or ECM product. For example, nitric oxide may be purchased, e.g. in a gas cylinder, or prepared separately, and the nitric oxide gas is then bubbled through, or otherwise diffused or mixed into a solution containing the tissue or ECM product. In another example, a solution comprising an ROS is first prepared and is then applied to tissue or an ECM product. In yet another example, the tissue or ECM product is mixed with reagents, such as Fenton's reagent for production of an ROS or RNS. In aspects, in the Fenton's reaction, hydrogen peroxide is reacted with d-metal ions (transition metal ions) to produce, among other products, hydroxide radicals (OH.). A similar Fenton's reaction can occur with nitrite where d-metal ions catalyze the formation of NO. The archetypical Fenton's reaction uses ($Fe(II)^{2+}$) with $H_2O_2$ according to the following: $Fe^{2+}+H_2O_2 \rightarrow Fe^{3+}+OH^-+OH.$, and therefore the archetypical Fenton's reagent is a mixture comprising Fe(II) ions, e.g., as Iron(II) sulfate, and $H_2O_2$. In the reaction, Fe(II) ions are oxidized to Fe(III) ions by the $H_2O_2$, producing hydroperoxyl radicals (HOO.). Other transition metal ions (d-metal ions, also referred to as d-block metal ions) can be used to catalyze production of radicals in "Fenton-like" reactions, including "catalyzed $H_2O_2$ propagations (CHP), such as Fe(II), Cu(I), Mn(II), V(II), Co(II), Cr(II), Ru(II), Ni(II) and Ti(III) (see, e.g. Goldstein, S., et al. "The Fenton Reagents" *Free Radic Biol Med.* 1993 Oct; 15(4):435-45). Other ions that can catalyze ROS and RNS production include $Ce^{3+}$ and $Ln^{2+}$ (See, e.g., Chumakov, A. et al. "Electro-Fenton-like Reactions of Transition Metal Ions with Electrogenerated Hydrogen Peroxide" *AIP Conference Proceedings* 1772, 040004 (2016); doi: 10.1063/1.4964563). Ions are provided in the form of salts, such as chloride or perchlorate salts.

Nitric oxide can be prepared by mixing dilute nitric acid with copper:

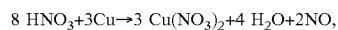
$$8\ HNO_3 + 3Cu \rightarrow 3\ Cu(NO_3)_2 + 4\ H_2O + 2NO,$$

or by reduction of nitrous acid in the form of sodium nitrite or potassium nitrite, e.g., as indicated in the following:

$$2\ NaNO_2 + 2\ NaI + 2\ H_2SO_4 \rightarrow I_2 + 4\ NaHSO_4 + 2\ NO$$

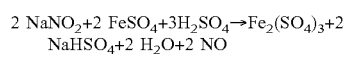
$$2\ NaNO_2 + 2\ FeSO_4 + 3H_2SO_4 \rightarrow Fe_2(SO_4)_3 + 2\ NaHSO_4 + 2\ H_2O + 2\ NO$$

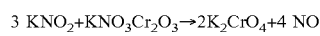
$$3\ KNO_2 + KNO_3Cr_2O_3 \rightarrow 2K_2CrO_4 + 4\ NO$$

In further aspects, ROS can be generated in water by photoilluminated metal oxides, such as $TiO_2$, ZnO, $V_2O_5$, $CeO_2$, $Fe_2O_3$, and $Al_2O_3$ (see, e.g., Wang, D. et al. "Quantitative Analysis of Reactive Oxygen Species Photogenerated on Metal Oxide Nanoparticles and Their Bacteria Toxicity: The Role of Superoxide Radicals" (2017) *Environ. Sci. Technol.* 51(17):10137-10145). This method can be utilized to produce ROS in water for use in the methods provided herein.

Peroxynitrite ($ONOO^-$) may be prepared by any method, for example and without limitation, by the reaction with a nitrite, such as isoamyl nitrite, with $H_2O_2$ ($H_2O_2 + NO_2^- \rightarrow ONOO^- + H_2O$).

In aspects, exposure of an ECM material to NO gas in air or other gaseous environment will be effective to cause S-nitrosylation of proteins within the ECM material.

Exposure of proteins, such as ECM proteins, results in formation of unique moieties within the proteins. ROS exposure leads to the production of protein carbonyl moieties, such as, without limitation, formation of glutamic semialdehyde, aminoadipic semialdehyde, 5-oxoproline, and 2-amino-3-ketobutyric acid moieties, from arginyl, lysyl, prolyl, or threonyl amino acid R-groups, respectively. As such, an ECM product prepared according to the methods described herein, and exposed to ROS, includes at least a two-fold (2×) increase, e.g., at least a 2×, 3×, 4×, 5×, 6×, 7×, 8×, 9×, or 10× increase in protein carbonyl moieties as compared to the tissue from which the ECM product is prepared, or ECM material prepared in the same manner, but not contacted with the ROS. In aspects, there is at least a 2×, 3×, 4×, 5×, 6×, 7×, 8×, 9×, or 10× increaseincrease in protein carbonyl moieties as compared to the tissue prior to contact with the ROS. Methods for detection and quantification of protein carbonyl groups are known to those of skill in the art. In aspects, a common method useful in detection of protein oxidation, as measured by the presence of protein carbonyl groups, involves derivatization of the carbonyl group with 2,4-dinitrophenylhydrazine (DNPH), which leads to formation of a stable dinitrophenyl (DNP) hydrazone product. This then can be detected by various means, such as spectrophotometric assay, enzyme-linked immunosorbent assay (ELISA), and one-dimensional or two-dimensional electrophoresis followed by Western blot immunoassay. Such assays are commercially-available, e.g., the Protein Carbonyl Content Assay Kit, commercially available from Abcam, of Cambridge, Massachusetts RNS exposure leads to the production of nitrotyrosine and nitrocysteine. As such, an ECM product prepared according to the methods described herein, and exposed to RNS, includes at least a two-fold (2×) increase, e.g., at least a 2×, 3×, 4×, 5×, 6×, 7×, 8×, 9×, or 10× increaseincrease in protein nitrotyrosine or nitrocysteine moieties as compared to the tissue from which the ECM product is prepared, or ECM material prepared in the same manner, but not contacted with the RNS. In aspects, there is at least a 2×, 3×, 4×, 5×, 6×, 7×, 8×, 9×, or 10× increaseincrease in protein nitrotyrosine or nitrocysteine moieties as compared to the tissue prior to contact with the RNS. S-nitrosylation of cysteine thiols can be detected by first blocking free sulfhydryl groups, and then selectively reducing nitrosylated cysteines and labeling them with a detectable reagent, such as biotin or other labels. Detection can be made by, for example, western blot or by other suitable immunodetection methods. Assays for S-nitrosylation are commercially available, such as the Pierce™ S-Nitrosylation Western Blot Kit, available from ThermoFisher Scientific. Nitrotyrosine moieties can be detected and quantified by a number of methods, but immunodetection methods are prevalent in light of the availability of anti-nitrotyrosine antibodies. For example, a competitive ELISA assay may be used to quantify nitrotyrosine in a sample, or anti-nitrotyrosine antibodies can be used to immunostain ECM products. Nitrotyrosine assays are commercially available, for example and without limitation, the Nitrotyrosine ELISA Kit, available from Cell Biolabs, Inc. of San Diego, California, and The chemiluminescent Nitrotyrosine Assay Kit, available from EMD Millipore of Burlington, Massachusetts In aspects, an ECM product is provided that is the product of the methods described herein, having increased protein carbonyls as compared to ECM product of the same tissue that is not treated with an ROS, such as at least a 2×, 3×, 4×, 5×, 6×, 7×, 8×, 9×, or 10× increaseincrease in protein carbonyl moieties as compared to the tissue from which the ECM product is prepared, or as compared to ECM material prepared in the same manner, but not contacted with the ROS. In aspects, there is at least a 2×, 3×, 4×, 5×, 6×, 7×, 8×, 9×, or 10× increaseincrease in protein carbonyl moieties as compared to the tissue prior to contact with the ROS. For ECM product contacted with an RNS, the ECM product has increased protein nitrotyrosine or nitrocysteine moieties as compared to ECM product of the same tissue that is not treated with an RNS. In aspects the ECM product includes at least a two-fold- (2×) increase, e.g., at least a 2×, 3×, 4×, 5×, 6×, 7×, 8×, 9×, or 10× increaseincrease in protein nitrotyrosine or nitrocysteine moieties as compared to the tissue from which the ECM product is prepared, or as compared to ECM material prepared in the same manner, but not contacted with the RNS. In aspects, there is at least a 2×, 3×, 4×, 5×, 6×, 7×, 8×, 9×or 10× increaseincrease in protein nitrotyrosine or nitrocysteine moieties as compared to the tissue prior to contact with the ROS. By increase in either protein carbonyl, protein nitrotyrosine, or protein nitrocysteine it is meant an increase in the number of protein carbonyl, protein nitrotyrosine, or protein nitrocysteine moieties for any given protein in the sample, or for overall protein content in the ECM product or overall mass of the ECM product.

Uses for the described materials, such as for treating a patient, e.g., methods of treating a patient are provided. In aspects, the patient has a wound, defect, or other injury or abnormality that is amenable to repair by use of an ECM material as described herein. Sheets or the material, gels and/or liquids, ointments, lotions, sprays, or salves, comprising the ECM material may be used. The wound may be internal or external, and includes chronic wounds, such as diabetic ulcers, e.g., diabetic foot ulcers. In another aspect, a sheet of ECM material may be used to reinforce an abdominal wall defect or injury.

Exposure of lipids within the ECM material to ROS or RNS results in an increase in the abundance of oxidized lipid products in the case of ROS exposure, and nitrated lipid products in the case of RNS exposure. As such, an ECM product prepared according to the methods described herein, and exposed to ROS, includes at least a two-fold (2×) increase, e.g., at least a 2×, 3×, 4×, 5×, 6×, 7×, 8×, 9×, or 10× increase in oxidized lipid products, as compared to the tissue from which the ECM product is prepared, or ECM material prepared in the same manner, but not contacted with the ROS. In aspects, there is at least a 2×, 3×, 4×, 5×, 6×, 7×, 8×, 9×, or 10× increaseincrease in oxidized lipid products as compared to the tissue prior to contact with the ROS. As such, an ECM product prepared according to the methods described herein, and exposed to RNS, includes at least a two-fold- (2×) increase, e.g., at least a 2×, 3×, 4×, 5×, 6×, 7×, 8×, 9×, or 10× increaseincrease in nitrated lipid products as compared to the tissue from which the ECM product is prepared, or ECM material prepared in the same manner, but not contacted with the RNS. In aspects, there is at least a 2×, 3×, 4×, 5×, 6×, 7×, 8×, 9×, or 10× increaseincrease in nitrated lipid products as compared to the tissue prior to contact with the RNS. Oxidized lipid products include peroxides, aldehydes, ketones, epoxides, hydroxy compounds, or oligomers and polymers. Peroxides are typically the primary or initial product of exposure of lipids to ROS. Methods are broadly-known for identification and/or quantification of oxidized or nitrated lipid products. In aspects, a variety of methods can be used to identify the increased presence of peroxidation products, including iodometry (volumetric), spectroscopic methods, ferrous or iodide oxidation methods, and chromatographic methods. Likewise, secondary oxidation products can be identified and/or quantified by spectroscopic or chromatographic methods. Nitrated products also can be identified and/or by spectroscopic or chromatographic methods.

In aspects, for ECM material contacted with ROS, an ECM product is provided that is the product of the methods described herein, having increased oxidized lipid products as compared to ECM product of the same tissue that is not treated with an ROS, such as at least a 2×, 3×, 4×, 5×, 6×, 7×, 8×, 9×, or 10× increaseincrease in oxidized lipid products, such as peroxides, as compared to the tissue from which the ECM product is prepared, or as compared to ECM material prepared in the same manner, but not contacted with the ROS. In aspects, there is at least a 2×, 3×, 4×, 5×, 6×, 7×, 8×, 9×, or 10× increaseincrease in lipid oxidation products, such as peroxides, as compared to the tissue prior to contact with the ROS. For ECM product contacted with an RNS, the ECM product has increased nitrated lipid products as compared to ECM product of the same tissue that is not treated with an RNS. In aspects the ECM product includes at least a two-fold (2×) increase, e.g., at least a 2×, 3×, 4×, 5×, 6×, 7×, 8×, 9×, or 10× increase in nitrated lipid products as compared to the tissue from which the ECM product is prepared, or as compared to ECM material prepared in the same manner, but not contacted with the RNS. In aspects, there is at least a 2×, 3×, 4×, 5×, 6×, 7×, 8×, 9×, or 10× increase in nitrated lipid products as compared to the tissue prior to contact with the RNS. By increase in either oxidized lipid products or nitrated lipid products it is meant an increase in the number or amount of an oxidized lipid product or a nitrated lipid product in the sample, or for overall mass of the ECM product.

The ECM material described herein may be formed into a suitable shape or may be provided in sheet form, depending on the processing of the material. In one aspect, the ECM material is a sheet that can be used by itself, or may be laminated with another sheet material, such as a non-bioerodible polymer mesh, for use in a patient, such as for repair of an abdominal wall defect. When in liquid or gel form, the ECM material may be combined with a synthetic or natural polymer structure, such as a porous mesh, to form a hybrid device.

While constituents of a device may be combined in any manner, an expedient method of depositing two or more liquid constituents, so as to form a fibrous mat, is electrodeposition. Electrodeposition, e.g., electrospinning, is used to deposit the polymer composition and, optionally, the ECM gel and/or other liquid, gel, cell or other biological or therapeutic constituents, such as a mammalian blood product, media buffer solution, medium, drug products, antibodies, etc. In its simplest sense, electrodeposition is caused by the deposit of a liquid composition, such as polymer fibers in the case of electrospinning, onto a target surface. Electrospinning methods are well-known in the field of tissue engineering and are conducted essentially as described below. Electrospinning permits fabrication of structures that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy, or structures having varying anisotropy at different parts of the structure. These aligned structures can influence cellular growth, morphology and ECM production.

The process of electrospinning involves placing a polymer-containing fluid (for example, a polymer solution, a polymer suspension, or a polymer melt) in a reservoir equipped with a small orifice, such as a needle, pipette tip, metal tube, or other metal structure referred to herein as a nozzle and also can be referred to as a spinneret, and a metering pump, such as a syringe pump or a peristaltic pump. One electrode of a high voltage source is placed in electrical contact with the polymer-containing fluid or orifice, while another electrode is placed in electrical contact with a target (traditionally, typically a collector screen or rotating mandrel).

During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically-shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased (electrically-charged) so that the total voltage difference between the nozzle and the target is sufficiently large to cause effective electrodeposition, e.g., 20 kV, though other potentials and polarities are able to achieve effective electrodeposition, for example, between −2 and −20 kV. Optionally, a focusing ring with an applied bias (for example, 1 to 10 kV) can be used to direct the trajectory of the charged jet of polymer-containing fluid. Under certain conditions, for instance with solutions lacking sufficient viscosity and/or electrospun with certain tolerances, a fiber is not formed, but a spray is formed, depositing discrete droplets onto the target instead of a fiber. This is electrospraying.

Relative charges of the nozzle and electrodes may be the reverse polarity (e.g., with the target, target deposition axis or target deposition space, which typically is biased (electrically charged) between 2 to 10 kV, and the nozzle being charged between from −3 to −15 kV). As the charged jet of fluid travels towards the biased target, the solvent typically evaporates during mid-flight, leaving behind a polymer fiber on the biased target, at the target deposition axis, or within the target deposition space. If the fluid is a polymer melt, the molten polymer cools and solidifies in mid-flight and is collected as a polymer fiber on the biased target. As the polymer fibers accumulate on the biased target, a non-woven, porous mesh is formed.

The properties of the electrospun structures, e.g., elastomeric scaffolds, can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice to create different qualities of the article depending on the relative locations of the nozzle and the target, target deposition axis or target deposition space.

The properties of the electrospun structure may also be varied by changing the magnitude of the voltages applied to the electrospinning system. In one exemplary and non-limiting aspect, the electrospinning apparatus includes a nozzle biased to 12 kV, a target electrodes biased to −7 kV each, and one or more optional nozzles biased to 3-10 kV to allow for concurrent electrospinning of different polymer compositions, or electrospray of cell solutions, ECM material, liquids, liquids comprising therapeutic agent(s), blood products, etc. Examples of useful orifice diameters range from 0.1 to 2 mm (I.D.) and a useful target distances (distance from nozzle to axis of deposition) range from 1 to 17 cm. Other electrospinning conditions that can be varied include, for example and without limitation, the feed rate of the polymer solutions, the solution concentrations, the polymer molecular weight, the injectors—deposition target axis distance, as well as the nozzle—target axis relative positioning and trajectories, e.g., controlled via robotic control systems.

As indicated above, in certain examples, electrospinning is performed using two or more nozzles, wherein each nozzle is a source of a same or different polymer solution. The nozzles may be biased (electrically charged) with different biases or the same bias in order to tailor the physical and chemical properties of the resulting fiber matrix.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In the context of the present invention, the structure is produced by co-electrospinning a polymer suspension comprising a synthetic or natural polymeric component and a biological polymeric component, along with electrospraying a liquid or pre-gel ECM product as described herein and/or other liquid(s). Non-limiting examples of useful range of high-voltage to be applied to the polymer suspension is from 0.5 to 30 kV, from 5 to 25 kV, and from 10 to 15 kV.

An ECM product is sprayed (e.g., pressure sprayed) or electrosprayed concurrently with the electrospinning of the polymer(s). Likewise, any additional liquid component of the wet-electrospun layer(s) is sprayed or electrosprayed concurrently with the polymeric constituents.

Any natural or synthetic biocompatible, electrodepositable material may be combined with the ECM material. In certain illustrative examples below, the filaments are prepared from a urethane, for example, and without limitation, a poly(ester-urethane)urea (PEUU), which is synthesized using putrescine as a chain extender and two-step solvent synthesis method described. PEUU features include high elasticity and mechanical strength coupled with controllable biodegradative and cell-adhesive properties. The polymer composition has found use in a number of in vivo scenarios including as a cardiac patch, in prosthetic heart valves, in abdominal wall repair, and in vascular grafts. Alternative chemistries allow the polyurethanes to include added non-thrombogenic chemical moieties, and to use non-degradable polyurethanes as permanent structures not meant to be remodeled in situ. Additional biodegradable polymeric compositions are known in the art, and exhibit suitable strength and elasticity for use along with, or substituting for the described PEUU.

In aspects, focusing on biomedical usage, polymeric components suitable for the articles described herein are any polymer that is biocompatible and optionally is biodegradable. In certain non-limiting examples, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold, where applicable. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting example, the polymer composition comprises a biomacromolecular component derived from an ECM. For example, the polymer composition may comprise collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically-, chemically-, biochemically-, and/or proteolytically-labile group, non-limiting examples of which include an ester moiety, amide moiety, anhydride moiety, specific peptide sequences, and generic peptide sequences.

In certain aspects, degradable polymers used to make the articles described herein also release therapeutic agents when they are implanted in and degrade within the patient's body. For example, the individual building blocks of the polymers may be chosen such that the building blocks themselves provide a therapeutic benefit when released in situ through the degradation process. In one example, one of the polymer building blocks is putrescine, which has been implicated as a substance that causes cell growth and cell differentiation. In another aspect, therapeutic agents may be linked using any applicable chemistry, to the polymer composition so that it is released upon degradation of the polymer composition in situ, such as by a linker comprising an ester bond or another biodegradable linkage.

In certain aspects, the biodegradable polymers comprise homopolymers, copolymers, and/or polymeric blends comprising, without limitation, one or more of the following monomers: glycolide, lactide, caprolactone, dioxanone, and trimethylene carbonate. In other aspects, the polymer(s) comprise labile chemical moieties, non-limiting examples of which include esters and anhydrides, which can be useful in, for example and without limitation, controlling the degradation rate of the articles described herein.

Non-limiting examples of a bioerodible polymer useful for tissue growth scaffolds, hydrogels, or particles include: a polyacrylate or polymethacrylate, a polyacrylamide or polymethacrylamide, a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In other aspects, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly (glycolide-co-trimethylene carbonate), or poly(glycolide-co-trimethylene carbonate-co-dioxanone).

Non-limiting examples of natural bioerodible polymers useful for preparation of tissue growth scaffolds, hydrogels, or particles include proteins, glycosaminoglycans, and polysaccharides, such as, without limitation, cross-linked or non-cross-linked: heparin, alginate (alginic acid), guar gum, carboxymethylcellulose (CMC), hyaluronic acid, pullulan, carrageenan, pectin, acid modified chitosan, xanthan gum, agarose, chitosan, collagen, elastin, cellulose, hyaluronic acid, and gelatin, and a mixture of any of the foregoing. Synthetic and/or natural polymer compositions may be cross-linked by any of a large variety of known crosslinking methods, using any of the large variety of known cross-linkers, for example, gelatin and/or hyaluronan crosslinked with methacrylate to produce methacrylated gelatin and/or hyalyronan, e.g., by photocrosslinking.

Although bioerodible constituents may be preferred, non-bioerodible polymers may be used that either do not erode substantially in vivo or erode over a time period of greater than two years. Compositions such as, for example and without limitation, polytetrafluoroethylene (PTFE), poly (ethylene-co-vinyl acetate), poly(n-butyl methacrylate), poly(styrene-b-isobutylene-b-styrene), and polyethylene terephthalate are considered to be non-bioerodable polymers. Other suitable non-bioerodable polymer compositions are broadly known in the art, for example, in stent coating and transdermal reservoir technologies. The growth scaffolds described herein may comprise a non-erodible polymer composition.

For uses that do not involve tissue engineering or biocompatibility, virtually any polymer composition amenable to the electrospinning process can be used to prepare the filamentous articles, and branched filamentous articles described herein, and any particles, solutions, liquids, etc. may be co-electrodeposited with the filaments.

With respect to polymer synthesis, diamines, diols, and diisocyanates are useful building blocks for preparing certain of the polymer compositions described herein. Diamines as described above have the structure $H_2N$—R—$NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as poly-caprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is, e.g., an aliphatic or aromatic hydrocarbon or a hydrocarbon comprising aromatic and aliphatic regions. The hydrocarbon may be linear or branched.

In additional aspects, the polymer composition may include polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and also is stiffer. TPA scaffolds structures are made essentially in the manner described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, Poly(DTE-co-27.5 DT succinate) is used. TPAs and methods of making TPAs are described, for example, in U.S. Pat. No. 5,216,115 and United States Patent Application Publication No. 2011/0082545, each of which is incorporated herein by reference for its technical disclosure, disclose useful TPAs.

In further aspects, methods are provided herein for treatment of wounds, injuries, or defects such as congenital defects, traumatic injuries, surgical wounds, etc., comprising administering an ECM product prepared as described herein by contacting tissue or an ECM material with an ROS or an RNS. The material, alone, or in the form of a devices, such as a mesh coated with the described ECM product, a cell growth matrix comprising the ECM product, a sheet of the ECM product, a powder or particulates, a liquid or gel comprising the ECM product, or a shape or prosthesis comprising the ECM product. The ECM product-containing composition or device is administered at or adjacent to a site of a wound, injury or defect, in an amount able to support growth of tissue at the site of the wound, injury, or defect. Injuries, such as abdominal wall injuries or defects can be treated with the ECM product according to any aspect described herein. In one aspect, a sheet or mesh of a bioerodible or non-bioerodible polymer is combined with a sheet of the ECM product to provide additional strength to the ECM product. In other aspects, a sheet or mesh of a bioerodible or non-bioerodible polymer is coated with a liquid or gel comprising solubilized ECM product as described herein. Chronic wounds are amenable to treatment with the ECM product in any form, including a sheet or a liquid or gel comprising solubilized ECM product as described herein. Chronic wounds include, for example, epithelial, granulation, slough, and eschar type wounds, examples of which including diabetic ulcers, venous stasis ulcers, arterial ulcers, pressure ulcers, traumatic ulcers, and post-surgical wounds. In other aspects, an ECM product described herein is used to treat an ischemic injury, such as, without limitation, treatment of atherosclerosis, stroke, myocardial infarction, or osteoarthritis. In aspects, an ECM product described herein is used for reconstructive surgery including, without limitation, vascular and nerve repair, hernia repair, breast reconstruction, pelvic organ reconstruction, reconstruction following cancer treatment, reconstruction following radiation treatment, repair of traumatic wounds, such as brain injury, spinal cord injury, or treatment of burns, etc. In further aspects, the ECM product can be used for treatment of a wound, injury, or defect that results from or is related to a degenerative disease, such as a neurodegenerative disease, including a neurodegenerative disease affected by oxidative stress, such as multiple sclerosis, Alzheimer's disease, or Parkinson's disease. As shown in below, increased GAG staining is seen at 90 days, therefore the materials described herein would, in aspects, be useful for repair, replacement, or regeneration of cartilage, such as knee cartilage.

Compositions and devices comprising the ECM products as described herein may be packaged, stored, and delivered in any suitable container, and in any suitable state. In one instance, the ECM product is dried, e.g. lyophilized, and is packaged in a suitable container, such as a foil or plastic pouch, and if subsequently comminuted, in a suitable tube, medical syringe, or other vessel. The ECM product also may be shipped in a hydrated state, likewise packaged in a suitable vessel, tube, medical syringe, or pouch. Liquid or pre-gel materials may be contained within suitable reservoirs for use in electrospraying.

EXAMPLE

The following shows that reactive oxygen and nitrogen species can serve as effective reagents for the decellularization of extracellular matrix biomaterials. These methods imbue biomolecular modifications that are characteristic of natural inflammatory reactions. The modification of extracellular matrix biomaterials with these highly reactive RNS and ROS result in a greater macrophage infiltration and a shift toward anti-inflammatory and anti-oxidant macrophage phenotypes in vitro and in vivo. Chronic remodeling resulted in enhanced production of glycosaminoglycans which can aid in beneficial wound healing.

Methods
Scaffold Preparation

Porcine small intestine was purchased from local slaughterhouse (Thoma Meat Market, Saxonburg, PA). Porcine small intestine submucosa was harvested through mechanical delamination of the external muscularis and internal mucosa layers. Native submucosa was cut into 1 foot lengths and then washed in DI $H_2O$ until water was no longer discolored by the tissue. Samples were decellularized using standard peracetic acid wash or nitric oxide, hydroxyl radical or both at washes for 2 hours followed by several washes with 1× PBS and water (B.M. Sicari, et al., The effect of source animal age upon the in vivo remodeling characteristics of an extracellular matrix scaffold, *Biomaterials*33(22) (2012) 5524-33), decellularizing with 0.1% PAA followed by multiple rinses with saline and water). Exemplary solutions include:

75 mM Sodium nitrite/15 mM iron (II) sulfate/30 mM sulfuric acid for nitric oxide; 15 mM Peracetic acid/15 mM iron(II) sulfate for hydroxyl radical; and 75 mM sodium nitrite/15 mM iron(II) sulfate/30 mM sulfuric acid/15 mM peracetic acid for peroxynitrite.

As nitric oxide and hydroxyl radicals will quickly react into other reactive nitrogen and oxygen species, decellularization methods will be described as RNS, ROS or RNS+ROS as the full range of species present was not characterized. Samples were then washed twice with 1XPBS then twice with water for 30 mins each. Decellularized scaffolds were frozen at −80° C. and then lyophilized. Samples used for implantation were terminally sterilized with ethylene oxide. ECM degradation products were produced using a 1 mg/mL pepsin solution in 0.01N HCl under constant stir for 48 hrs to create a 10 mg/mL ECM digest.

Scaffold Characterization

Hydrated native tissue and decellularized scaffolds were fixed in 10% neutral buffered formalin (NBF) and then embedded in paraffin. Sections of these scaffolds were stained separately with hematoxylin & eosin or DAPI to confirm removal of nuclei. Proteinase K digests of native whole small intestine, native submucosa and decellularized scaffolds underwent phenol: chloroform: isoamyl alcohol (25:24:1) extraction for DNA and were resuspended in 1× TE buffer. Native submucosa was used as a control in addition to whole small intestine as the submucosa is the layer used for biomaterial preparation. DNA extracts were separated using electrophoresis on a 2% agarose gel in 0.5α TBE buffer to confirm reduction of DNA content and fragmentation of remnant DNA in decellularized scaffolds compared to native controls. DNA extracts were also quantified for double-stranded DNA content using a PicoGreen assay (Thermo) according to manufacturer's instructions.

Biochemical Analysis

ECM scaffold biochemistry was performed to assess hydroxyproline and sulfated glycosaminoglycan content. Native small intestine, native small intestine submucosa, and decellularized ECM scaffolds were digested at 10 mg/mL in a papain solution. Sulfate glycosaminoglycan content was assessed using a dimethylmethylene blue (DMMB) reagent. Hydroxyproline content was assessed by adding 50 pL 2N NaOH to 50 pL papain digests then hydrolyzing at 110° C. for 18 hrs. Samples were neutralized with 5N HCl. One hundred microliters of 0.01 M copper sulfate, 2.5 N NaOH and 6% $H_2O_2$ were added. Samples were incubated at 80° C. for 5 minutes then cooled. Four hundred microliters of 3 N sulfuric acid was added followed by 200 pL of 5 % DMAB in propanol. Samples were incubated at 70° C. for 15 minutes then the absorbance was read at 540 nm. Protein carbonyl content, a marker of oxidation, was determined using a kit from Cayman Chemical as per manufacturer instructions.

Immunohistochemical Analysis

Native and decellularized SIS was fixed in 10% NBF then embedded in paraffin wax. Sections were stained using DAB immunohistochemistry for markers of nitrosylation or oxidation, including 5-nitro-cysteine, 3-nitro-tyrosine and cysteine sulfonate. Briefly, paraffin sections were deparaffinized to water then antigen was retrieved using 10 mM citric acid pH6 0.05% Tween20 for 20 mins at 95-100° C. Slides were washed twice with 1× TBST for 5 mins then twice with 1XPBS for 3 mins. Endogenous peroxidase activity was blocked by incubating slides in 0.3% hydrogen peroxide for 30 mins. Slides were washed 3 times in 1× PBS for 3 minutes. Slides were blocked for non-specific antibody binding with a blocking buffer made of 2% donkey serum/ 1% bovine serum albumin/0.1% Tween-20 for 1 hour at room temperature. Primary antibodies (1:500 5-nitrocysteine (abcam 94930), 1:200 nitrotyrosine (abcam 7048), or 1:100 cysteine sulfonate (Enzo ADI-OSA-820-D) were incubated overnight at 4° C. diluted in blocking buffer. Slides were washed 3 times for 3 minutes with 1×PBS Slides were then incubated with biotinylated secondary antibodies diluted in blocking buffer (goat anti-mouse or goat anti-rabbit 1:200 (Vector)). Slides was again 3 times for 3 minutes with 1×PBS Slides were incubated with VectaShield ABC Reagent for 30 mins then washed again 3×3 mins with 1×PBS. Staining was developed by incubating sections with 4% DAB (Vector). Sections were washed then mounted with resinous mounting media and coverslipped. Slides were images on a brighfield microscope at the same settings.

Macrophage Isolation

Bone marrow-derived macrophages were harvested from 2 month or 18-20 month-old C57/BL6 mice as previously described [8]. Briefly, femurs and tibiae were harvested and separated from muscle and connective tissue. Bones were cut at either end to expose bone marrow. Sterile syringe and needles were used to flush out bone marrow using macrophage differentiation media (DMEM/10% FBS/10% L-929 Supernatant/1% PenStrep/2% MEM non-essential amino acids/1% HEPES/0.1% 55 µM β-2 mercaptoethanol). Bone marrow lysate was reconstituted in media and filtered through a sterile cell filter. Cells were cultured for 7 days in media to differentiate them into macrophages, changing differentiation media every 2 days.

Macrophage Treatment

Following 7 days of differentiation culture as described above, macrophages were treated with acute polarizing regimens to distinguish phenotypes over 24 hours. Naïve macrophage (MO) controls were treated with basal media for 24 hours. M1 (20 ng/mL IFN-γ and 100 ng/mL LPS) and M2 (20 ng/mL IL-4) (Peprotech) polarizing cytokines were used to create positive controls for classical pro- and anti-inflammatory macrophages. ECM degradation products were neutralized and diluted to 1000 pg/mL in macrophage media to isolate biochemical effects of degradation products and prevent structural moieties from forming. Pepsin buffer (1 mg/mL pepsin in 0.01 M HCl) diluted in macrophage media was used as a control. Another set of treatment groups involved 24-hour exposure of ECM degradation products followed by 24-hour treatment with either the M1 or M2 treatment regimen. These experiments were performed to assess the effect of ECM exposure upon the ability of macrophages to polarize to classical M1 and M2 phenotypes.

Indirect Immunofluorescent Antibody Staining

Cells were fixed with 2% paraformaldehyde (PFA) for 30 minutes then washed in 1×PBS Cells were incubated in blocking buffer (2% donkey serum (Lampire), 1% bovine serum albumin (BSA) (Sigma), 0.1% Tween-20 (Fisher)) for 1 hour at room temperature. Primary antibodies were diluted in this blocking buffer as follows and incubated overnight at 4° C.: iNOS (1:100, Abcam 3523), Arginase-1 (1:200, Abcam 91279), or heme oxygenase-1 (1:200, Abcam ab13243). iNOS is a classical M1 macrophage marker whereas Arginase-1 is a classical M2 macrophage marker [33]. Heme oxygenase-1 is an anti-oxidant marker upregulated by macrophages during oxidative stress [34]. Cells were washed in 1×PBS then incubated in the appropriate fluorescently-labeled secondary antibody solution in blocking buffer for 1 hour at room temperature (donkey anti-rat Alexa Fluor 488, Invitrogen, 1:200; donkey anti-rabbit Alexa Fluor 488, Invitrogen, 1:300). Cell nuclei were counterstained with 500 nM DAPI (Ebioscience) for 10 minutes. Cells from 2 month old mice were imaged nine times in the center of each well at 10× magnification using automated position capture function to remove bias from subjective image location acquisition. All imaging was performed on an Axio observer T1 microscope. Mean fluorescence intensity of cells was analyzed using Cell Profiler software (Broad Institute). Briefly, DAPI images were used by the program to identify cell nuclei then FITC images were used to identify cell borders around the identified nuclei. The mean fluorescent intensity was calculated by averaging the pixel intensities (scale of 0 to 1) across the entire cell area. Mean fluorescence intensity values were averaged for all imaged cells in each well.

Phagocytosis Assay

Following treatments, cells were assayed for phagocytic ability using Vybrant Phagocytosis Assay Kit (Invitrogen). Cells were incubated in FITC-labeled dead E. Coli particles for 2 hours in the cell culture incubator. Following washing, the cells were fixed with 2% PFA for 30 minutes then washed with 1X PBS. Cells were counterstained with DAPI then imaged and analyzed as described above.

Nitrite Assay

Following treatments, 50 pL of supernatant from macrophages were transferred into a fresh plate. Nitrite content was assayed using a Greiss Reagent system. Briefly, 50 pL of sulfanilamide (1% in 5% phosphoric acid) was added to supernatants for 10 minutes. Then, 50 pL of 0.1% N-1-napthylethylenediamine in water was added to the mixture for an additional 10 minutes. The absorbance at 540 nm was measured using a BioTek SYNERGY HTX spectrophotometer.

Arginase Activity Assay

Following treatments, media was removed and macrophages were lysed in 50 µL 0.001% Triton X-100 in type 1 H2O with 1× Halt Protease Inhibitors (Thermo). Twenty five microliters of lysate was added to 25 µL of arginase activation solution (10 mM MnC12/50 mM Tris-HCl, pH7.5) and incubated at 55° C. for 10 minutes. Samples were allowed to cool and then 50 µL of arginine substrate solution (0.5 M L-arginine pH 9.7) was added to each well. Samples were incubated at 37° C. for 2 hours. A urea standard curve was created via 2 fold serial dilution from 100 mg/mL to 1.5625 mg/mL with a 0 mg/mL blank in lysis buffer. Five microliters of samples or standards were added to a new 96-well plate and 200 pL of urea detection solution (513 mg/L primaquine, 100 mg/L phthalaldehyde, 2.5 mol/L sulfuric acid, 2.5 g/L boric acid, 0.03% Brij35) was added to each well. Absorbance of samples was analyzed using a plate spectrophotometer at 430 nm between 5-20 minutes following addition of detection solution.

Abdominal Wall Partial Thickness Defect Implantation

Four month old C57BL6/J mice (Jackson) were anesthetized using isofluorane and analgesized using Buprenex prior to surgical manipulation. Abdominal skin was incised and abdominal muscle exposed. Partial thickness defects (1 cm2 were created in the abdominal muscle by removing the external 2 of the 3 muscle layers. Rehydrated 1 cm2 muscle ECM scaffolds (n=5 per treatment) were sutured over the defect using 4-0 polypropylene sutures. Skin incisions were sutured close using 3-0 PGCL suture. This is a modification of an existing animal model for biomaterial host response evaluation [30]. Animals were maintained on Buprenex and Baytril for 3 days post-operation. ECM was explanted following 7 and 90 days post-implantation. Sections were fixed in 10% NBF for histologic analysis.

Histologic Analysis

Paraffin sections at 5 µm were stained for hematoxylin & eosin, Masson's trichrome, Alcian blue, Herovici's polychrome, and PicroSirius Red. Five images were taken per slide at 20× for quantitation using brightfield microscopy or circularly polarized light microscopy for PicroSirius Red. Acute time-points (7 days) were stained using immunofluorescent antibody labeling. Briefly, slides were deparaffinized then antigen retrieved using 10 mM citric acid at 95-100° C. for 20 mins. Autofluorescence was quenched using a 10 mM copper sulfate/50 mM ammonium acetate (pH5) solution for 20 mins at 37° C. Sections were blocked using 2% donkey serum/1% BSA/0.1% Tween-20 for 1 hour then incubated overnight at 4° C. with primary antibodies for F4/80 (1:100 BioRad MCA497), iNOS (1:100 Abcam 3523), Arginase-1 (1:200 Abcam 92179), or Heme oxygenase-1 (1:100, Abcam 13243). Sections were washed in PBS then incubated for 1 hour with the appropriate Alexa Fluor 488 donkey antibody at 1:200 (Abcam). Sections were washed, counterstained with DAPI then mounted with FluoroGel mounting solution.

Immunofluorescent stained slides were imaged 5 times per slide at 20× on a Nikon Eclipse TI-U and analyzed on Nikon Elements software. Mean fluorescence intensity of cells were analyzed using Cell Profiler software as described above. Ninety day explants were stained immunohistochemically for fast & slow myosin heavy chain using alkaline phosphatase and DAB solutions, respectively [35].

Statistical Analysis

Quantitative results were analyzed using a two-way ANOVA (treatment, age) with Tukey post-hoc analysis using GraphPad PRISM 7 software. Significance was determined at a p-value less than 0.05.

Results

Assessment of Decellularization

Histologic assessment of decellularization showed that all methods resulted in significant removal of nuclei (FIG. 1A, panels A-E (FIG. 1A (A-E)). Morphologically, ECM decellularized with PAA seemed to be more similar to native morphology whereas FR-decellularized ECM seemed to organize into thicker, irregular fiber bundles. Masson's trichrome staining appeared similar across decellularized ECM, suggesting similar levels of collagen content (FIG. 1A (F-J)). Alcian blue staining was also consistent, suggesting similar glycosaminoglycan content across decellularization methods (FIG. 1A (K-O)). Cysteine sulfonate staining, a marker of oxidation, only appeared to be weaker in the ROS decellularization method (FIG. 1B (P-T)). S-nitrocysteine immunohistochemistry showed higher staining with RNS and RNS+ROS decellularization methods, as expected (FIG. 1B (U-Y)). 3-nitrotyrosine immunohistochemistry also showed higher staining in RNS and RNS+ROS decellularization methods (FIG. 1B (Z-AD)). This suggests a higher presence of nitroxidative protein modifications within RNS and RNS+ROS decellularization protocols.

Biochemical Analysis

Figure 2A:
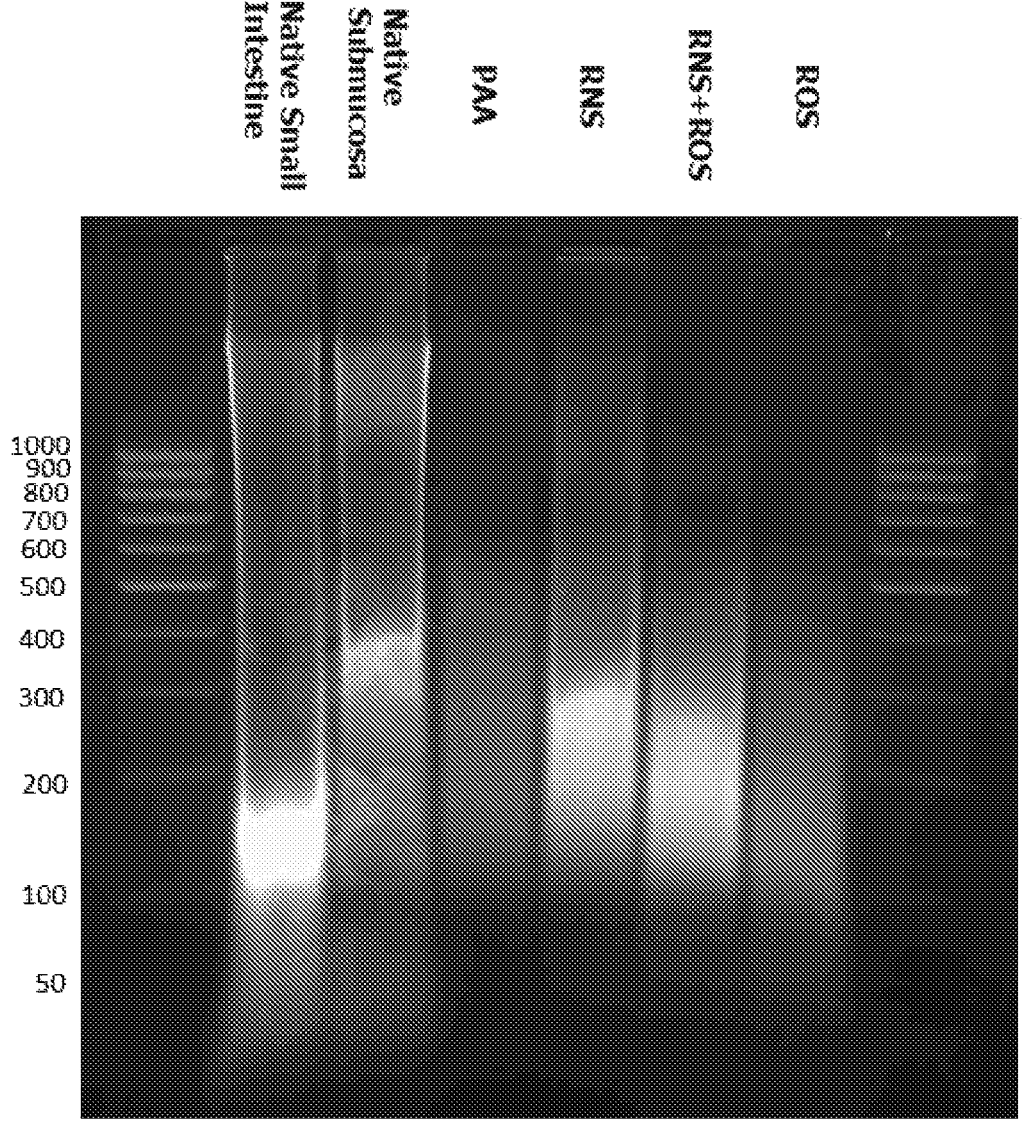
FIGS. 2A-2E: Biochemical assessment of DNA, hydroxyproline, glycosaminoglycan and protein carbonyl content. DNA agarose gel electrophoresis of DNA extracts from ECM (FIG. 2A). PicoGreen quantification of ds DNA content in ECM (FIG. 2B). Hydroxyproline (FIG. 2C), protein carbonyl (FIG. 2D) and DMMB glycosaminoglycan (FIG. 2E) assays for biochemical content. Results presented as mean ±S.D. (* represents $p<0.05$,  $p<0.01$, * $p<0.001$, **** $p<0.0001$).
Figure 2B:
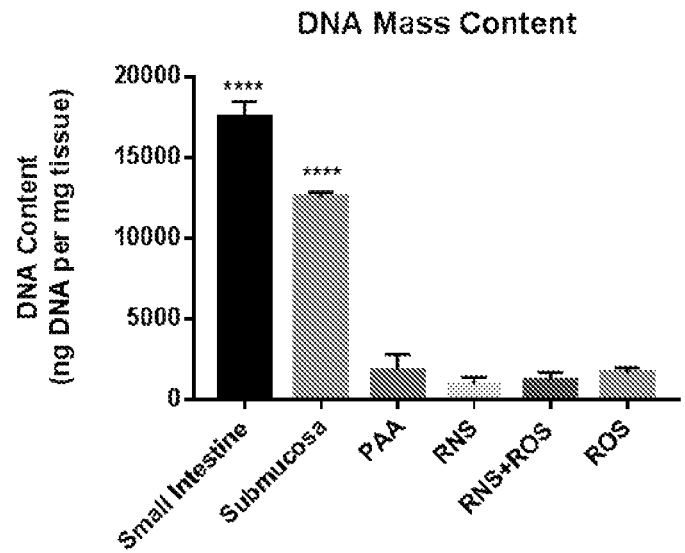

Biochemical assessment of native and decellularized scaffolds confirmed sufficient removal of cellular DNA content. Agarose gel electrophoresis showed significant fragmentation and removal of DNA from all decellularization methods (FIG. 2A). However, there seemed to be higher levels of small DNA fragments in the RNS and RNS+ROS decellularized samples. Despite this finding, double stranded DNA quantification showed no significant difference in the amount of DNA between any decellularization method (FIG. 2B). The dsDNA content in decellularization methods was reduced 90-95% from native small intestine and 86-93% from native submucosa. All methods resulted in dsDNA content less than 2000 ng/mg dry tissue.

Figure 2C:
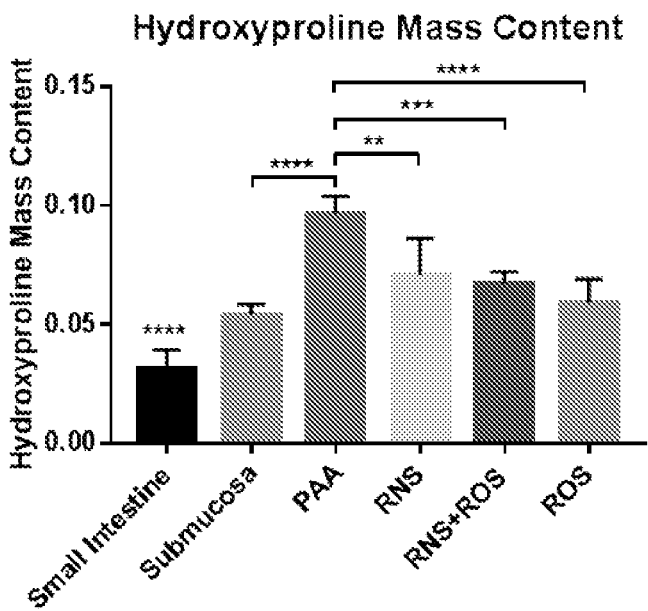
Figure 2D:
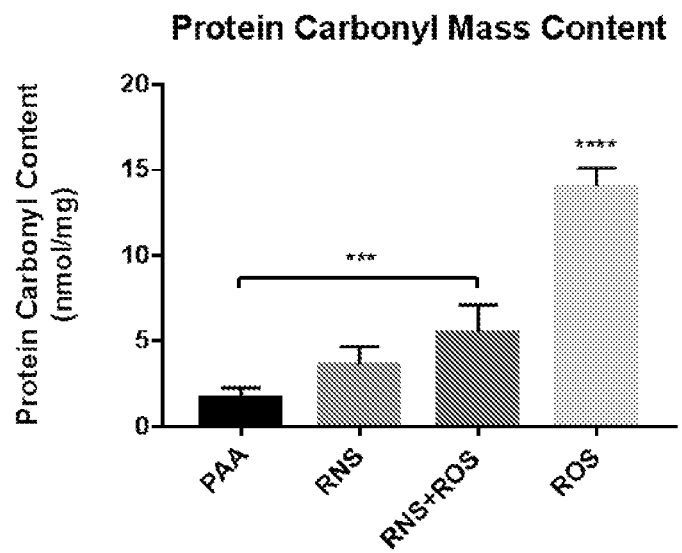
Figure 2E:
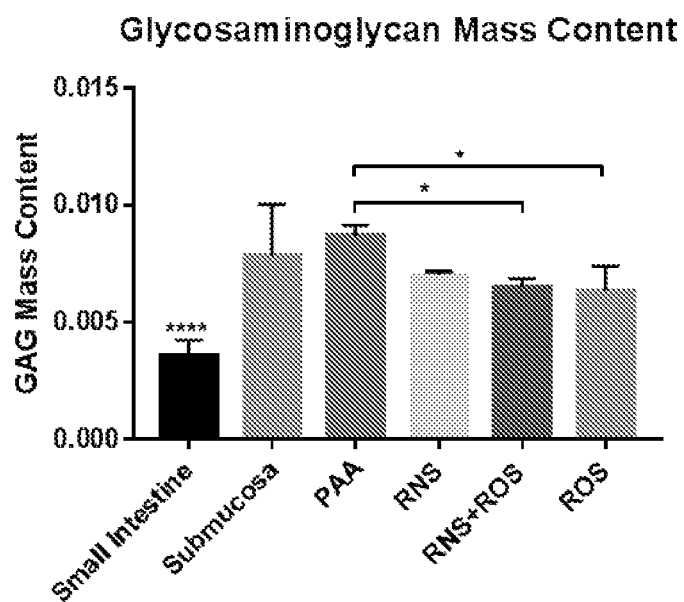
Figure 3A:
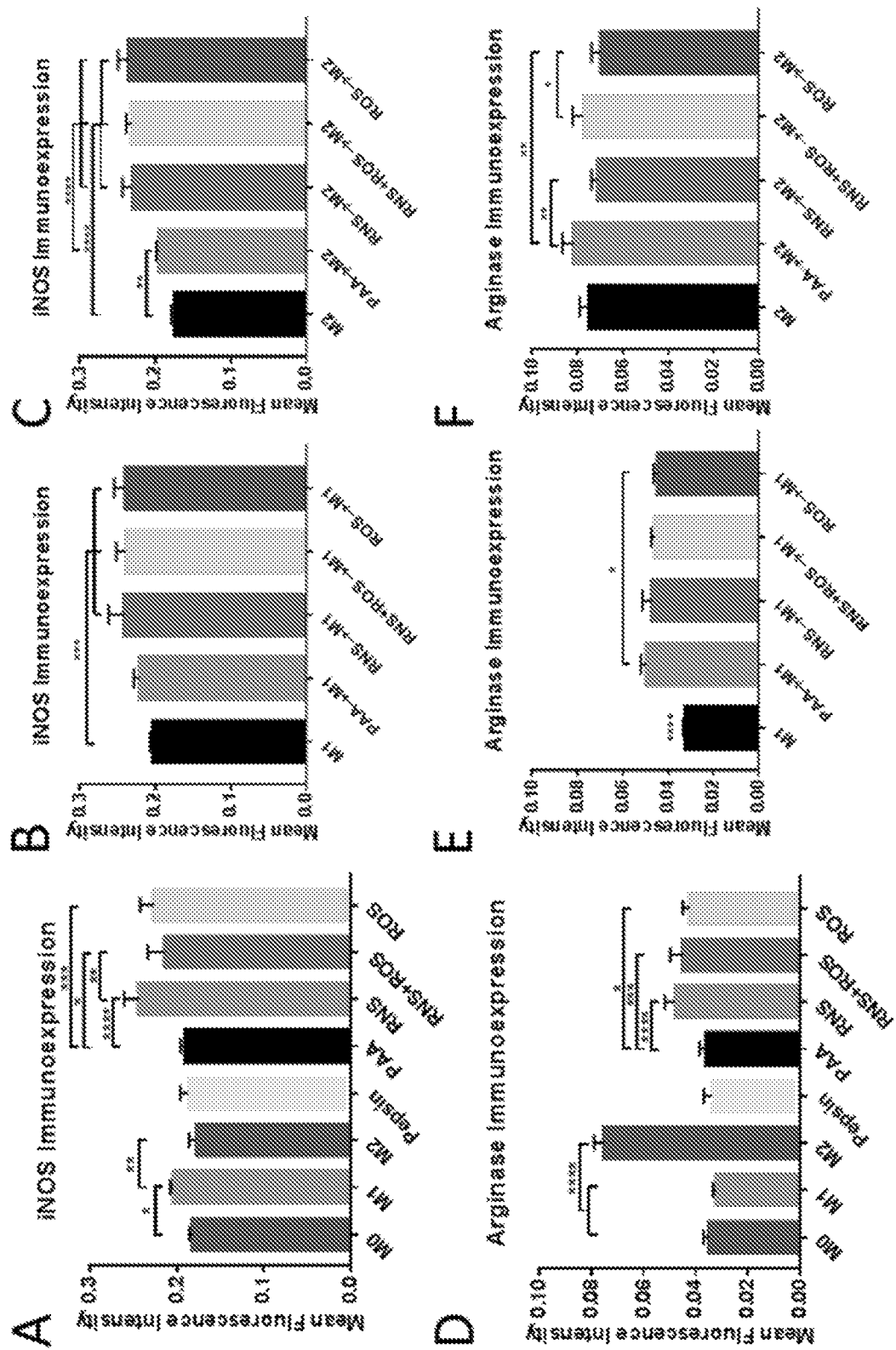
FIGS. 3A-3C: Bone marrow macrophage cultures with ECM pepsin digests. Immunofluorescence staining for iNOS (FIG. 3A (A-C)), arginase (FIG. 3A (D-F)) and HO-1 (FIG. 3B (G-I)). Greiss reagent system assessment of nitric oxide production in macrophage supernatants (FIG. 3B (J-L)). Urea production from arginase activity assay (FIG. 3C (M-O)). Results presented as mean ±S.D. (* represents $p<0.05$,  $p<0.01$, * $p<0.001$, **** $P<0.0001$).
Figure 3B:
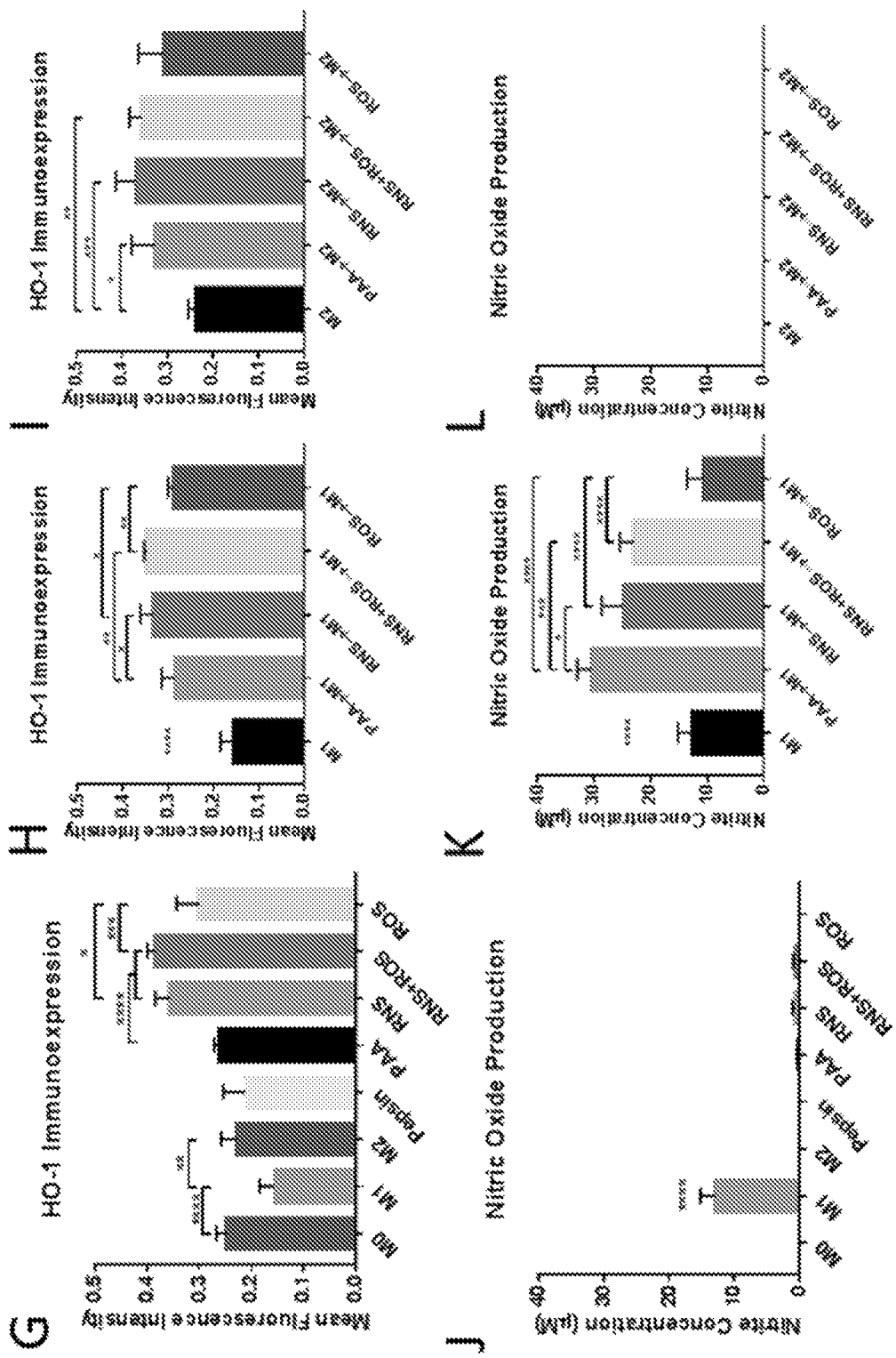
Figure 3C:
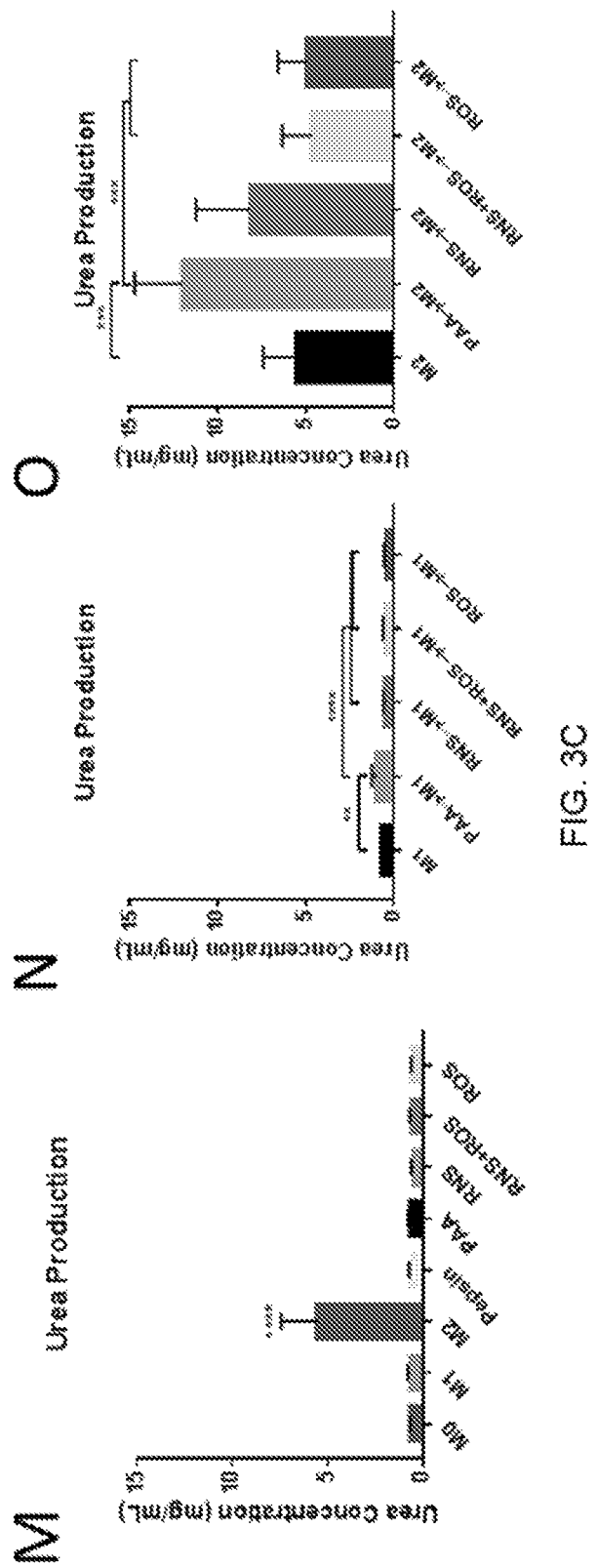

All decellularization methods resulted in an enrichment in hydroxyproline content. However, all FR methods resulted in a significant reduction in hydroxyproline content compared to PAA controls (FIG. 2C). Similarly, glycosaminoglycan content was enriched with decellularization but reduced from PAA to RNS+ROS and ROS scaffolds (FIG. 2E). RNS+ROS decellularization resulted in significantly higher protein carbonyl content compared to PAA controls while ROS scaffolds had higher protein carbonyl content than all other methods (FIG. 2D). This confirms that FR decellularization methods induced protein oxidation in all groups. In vitro macrophage response Murine bone marrow-derived macrophages were exposed to ECM degradation products in order to determine if radical inflammatory species decellularization altered the macrophage response to ECM. M1 controls which were exposed to IFN-γ and LPS had higher levels of iNOS immunoexpression and nitric oxide production, as well as reduced levels of heme oxygenase-1 immunoexpression (FIGS. 3A and 3B (A,G,J)). M2 controls treated with IL-4 had increased levels of arginase-1 immunoexpression and increased urea production (FIGS. 3A and 3C (D,M)). ECM controls treated with PAA had baseline levels of iNOS, arginase and HO-1 immunoexpression as well as no nitric oxide or urea production (FIGS. 3A-3C (A,D,G,J,M). All FR-decellularized ECM resulted in increased immunoexpression of iNOS, arginase-1 and heme oxygenase-1 compared to PAA controls (FIGS. 3A and 3B (A,D,G)). RNS ECM had higher levels of iNOS immunoexpression than RNS+ROS ECM (FIG. 3A (A)). ROS ECM had lower levels of heme oxygenase-1 than RNS and RNS+ROS ECM but was not different than PAA ECM (FIG. 3B (G)).

The effect of ECM exposure upon the ability of macrophages to polarize to extremes is important in understanding the mechanism of biomaterial promotion of altered host responses. Previous studies have shown that macrophage exposure to different types of extracellular matrix biomaterials have altered their phenotype and function following established cytokine polarization schemes [28]. Macrophages were exposed to ECM degradation products for 24 hours then exposed to M1 or M2 cytokines for the subsequent 24 hours. PAA ECM had no effect on iNOS immunoexpression with M1 stimulus but all FR ECM resulted in an increased iNOS immunoexpression level over M1 controls (FIG. 3A (B)). All ECM exposure resulted in significant increases in iNOS immunoexpression with IL-4 stimulus over M2 controls (FIG. 3A (C)). FR ECM with IL-4 post-stimulation resulted in a significant increase over PAA controls as well (FIG. 3A (C)). Arginase immunoexpression was significantly increased with IFN-γ/LPS stimulation over M1 controls (FIG. 3A (E)). ROS ECM also had significantly less arginase-1 immunoexpression compared to PAA ECM with M1 stimulation (FIG. 3A (E)). In the M2 stimulation group, no ECM treatment had different arginase immunoexpression than M2 controls (FIG. 3A (F)). ROS ECM elicited decreased arginase immunoexpression from PAA and RNS+ROS ECM while RNS ECM was lower than PAA ECM with IL-4 stimulus (FIG. 3A (F)). With M1 stimulus, all ECM groups resulted in increases in heme oxygenase-1 immunoexpression (FIG. 3B (H)). RNS and RNS+ROS ECM with M1 stimulus were higher than PAA and ROS ECM (FIG. 3B (H)). With IL-4 stimulus, PAA, RNS and RNS+ROS ECM resulted in significantly higher heme oxygenase-1 immunoexpression than M2 controls (FIG. 3B (I)). Nitric oxide production with M1 post-stimulus was higher with PAA, RNS and RNS+ROS ECM (FIG. 3B (K)). PAA ECM resulted in the highest nitric oxide production with IFN-γ/LPS while RNS and RNS+ROS was higher than ROS ECM (FIG. 3B (K)). There was not substantial nitric oxide production with any IL-4 stimulation condition (FIG. 3B (L)). Macrophages treated with IL-4 showed a significant increase in urea production as expected (FIG. 3C (M)). There were no significant induction of urea production with ECM treatment alone (FIG. 3C (M)). With IFN-γ/LPS stimulus, PAA-treated ECM increased urea production over M2 controls and FR-ECM (FIG. 3C (N)). With IL-4 stimulus, PAA ECM also increased urea production over M2 controls as well as RNS+ROS and ROS ECM (FIG. 3C (O)).

Histological Evaluation of In Vivo Host Response

Figure 4A:
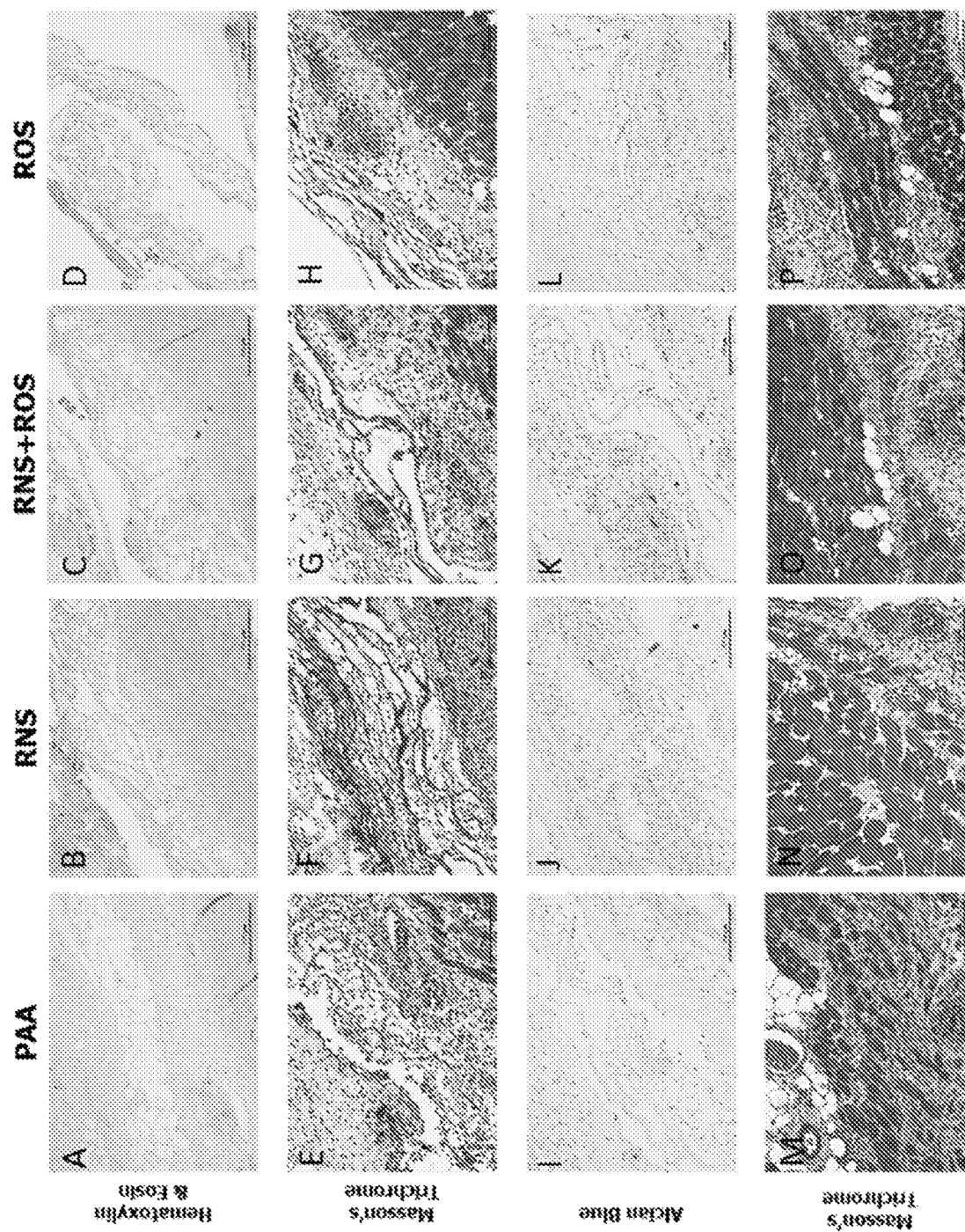
FIGS. 4A-4E: Histological assessment of explants from 7 day ECM repair of abdominal wall defect. Representative 20× images of hematoxylin & eosin (FIG. 4A (A-D)), Masson's trichrome (FIG. 4A (E-H)) and Alcian blue (FIG. 4A (I-L)) staining of 7 day explants of remodeling ECM. Masson's trichrome staining of regenerating muscle fibers (FIG. 4A (M-P)). Original
Figure 4B:
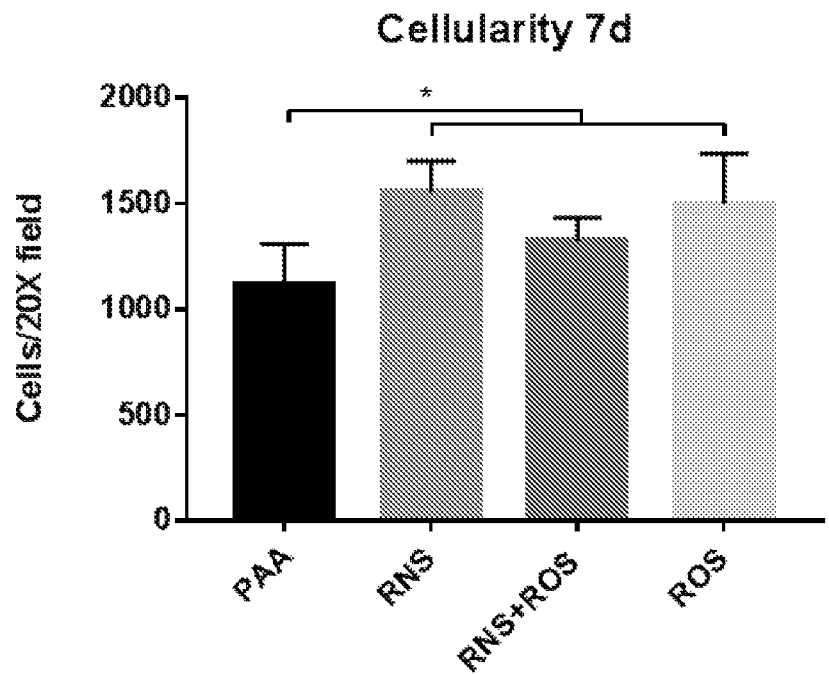
Figure 4C:
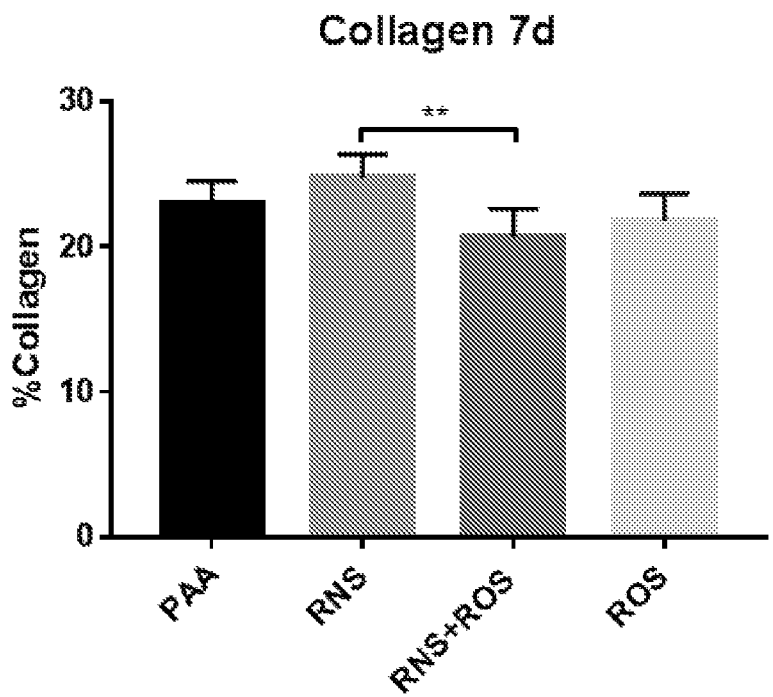
Figure 4D:
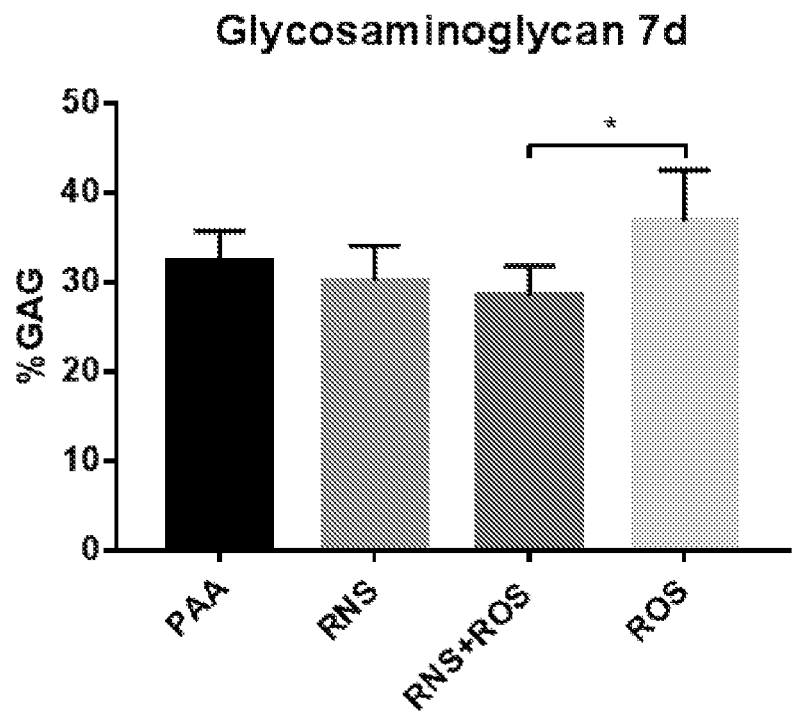
Figure 4E:
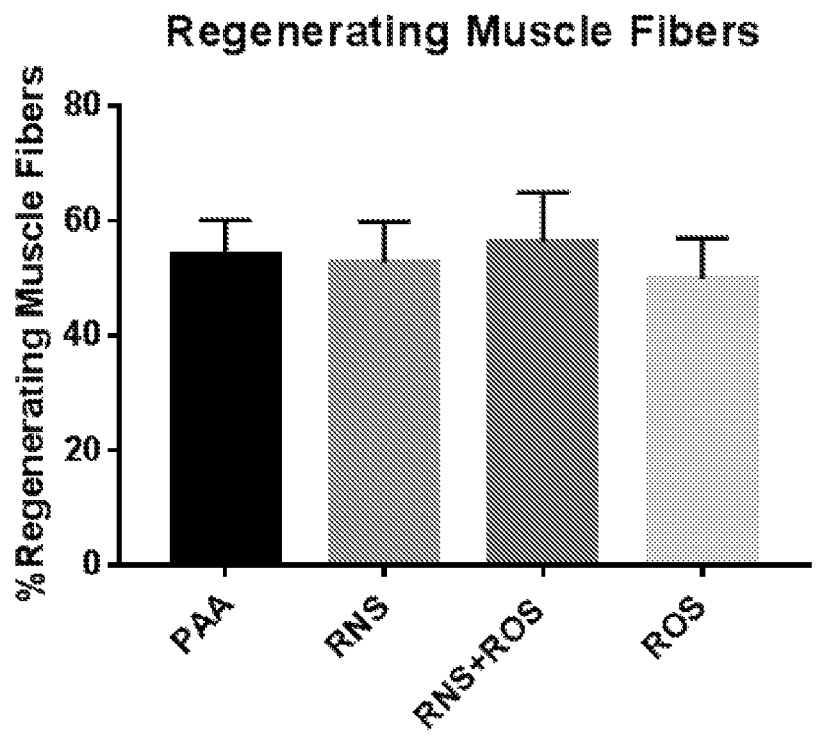

ECM scaffolds were used to repair a partial thickness defect of the abdominal wall in order to assess the host response to FR-decellularized ECM in vivo. This is a standard model which has been used extensively to assess the host response and remodeling of ECM scaffolds [7, 30, 31, 36]. Cellularity was assessed using hematoxylin & eosin staining (FIG. 4A (A-D)). RNS and ROS ECM exhibited an enhanced cellular infiltration at 7 days compared to PAA controls (FIG. 4B). This suggests the RNS and ROS modifications elicit higher levels of cellular migration to the wound site. Collagen content as assessed by Masson's trichrome staining did not show large changes at 7 days (FIG. 4A (E-H)). There was a significant decrease in Masson's trichrome staining with RNS+ROS ECM from RNS ECM (FIG. 4C). Glycosaminoglycan content, as assessed by Alcian blue staining, was similar in magnitude across groups (FIG. 4A (I-L)). ROS ECM explants at 7 days did result in significantly higher Alcian blue staining at 7 days compared to RNS+ROS ECM (FIG. 4D). Visual observation did not show any large differences in muscle fiber regeneration at 7 days (FIG. 4A (M-P)). There was no difference in the percentage of centralized nuclei in muscle fibers, indicating there was no difference in the regeneration of muscle fibers at 7 days (FIG. 4E). Overall, histologic assessment showed a more robust cellular infiltration from RNS and ROS ECM without substantial changes in broad ECM production.

Evaluation of In Vivo Macrophage Response

Figure 5A:
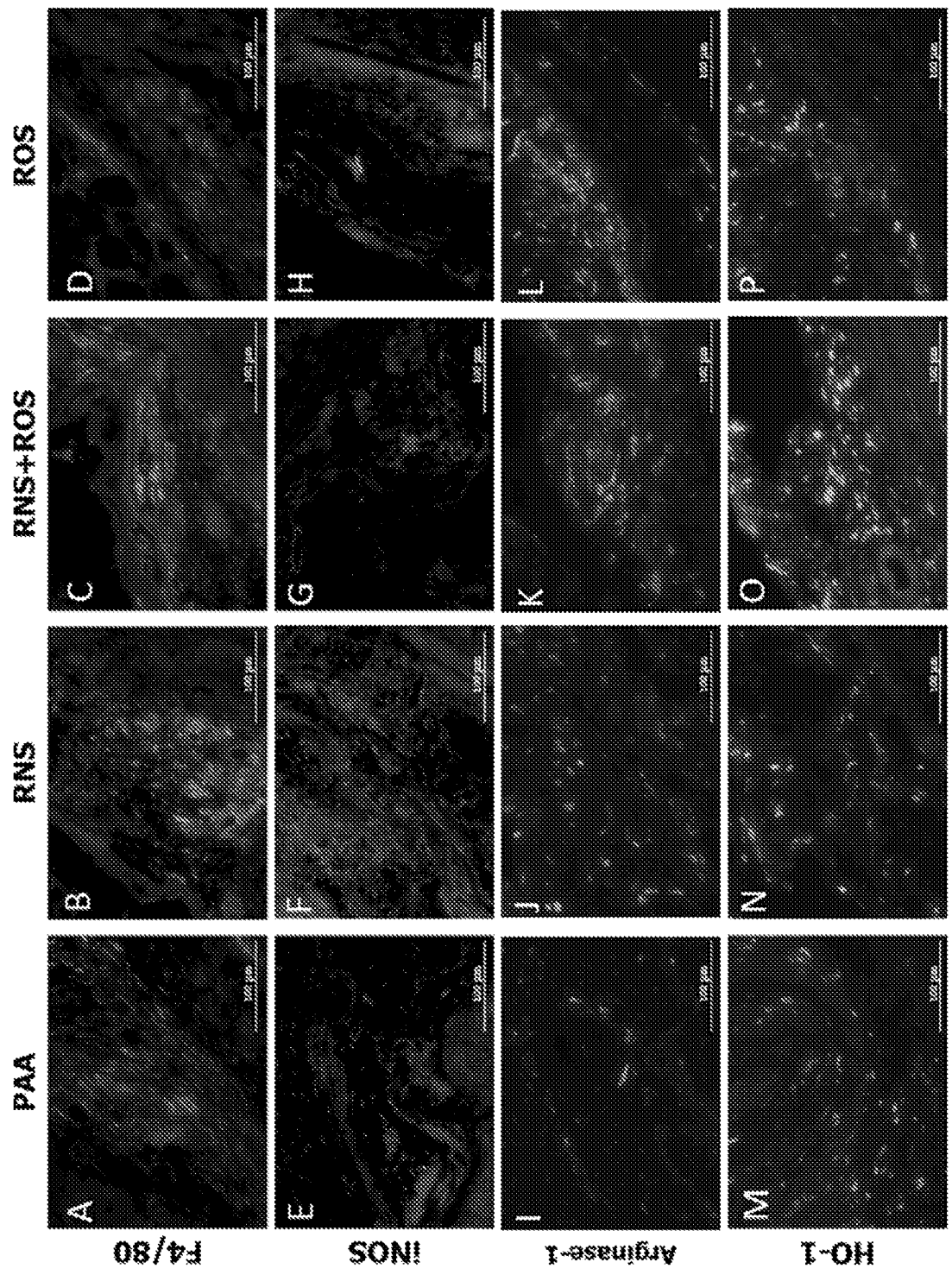
FIGS. 5A-5E: Immuno-labeling of 7 day explants for macrophage polarization markers. Representative 20× images of immunofluorescent staining of 7 day explants for F4/80 (FIG. 5A (A-D)), iNOS (FIG. 5A (E-H)), arginase-1 (FIG. 5A (I-L)) and heme oxygenase-1 (FIG. 5A (M-P)). Original
Figure 5B:
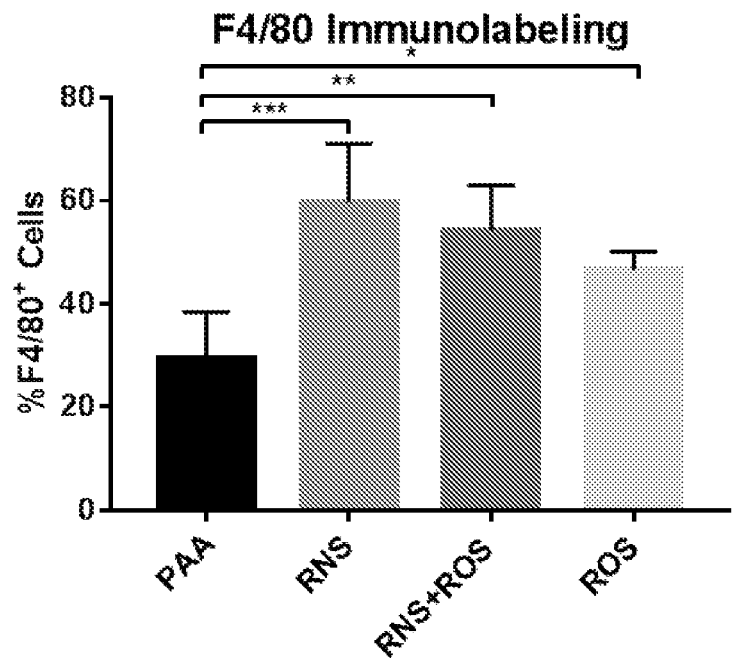
Figure 5C:
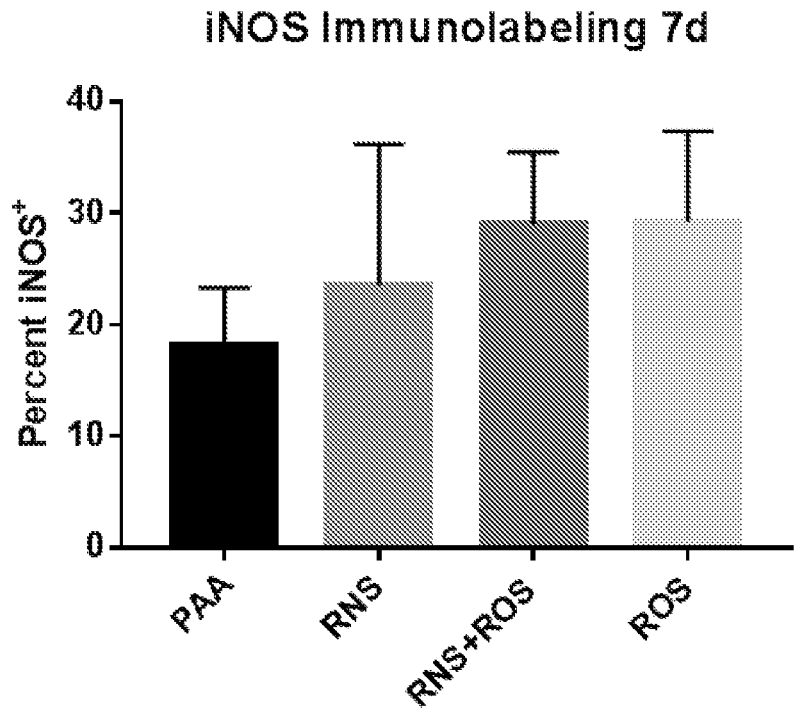
Figure 5D:
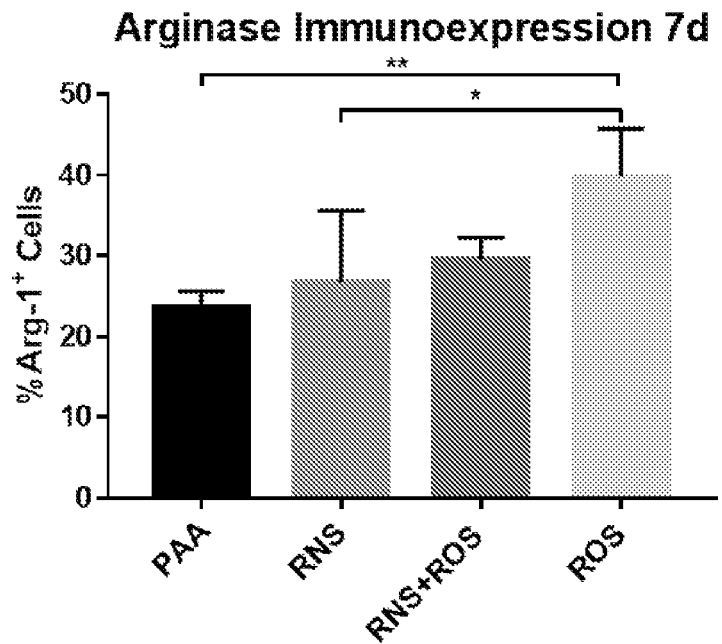
Figure 5E:
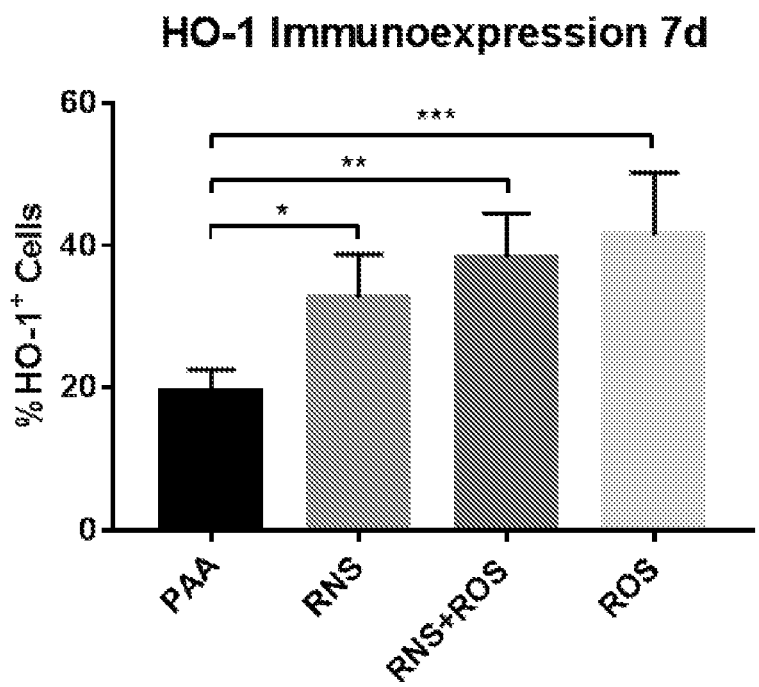

As macrophage phenotype at acute time-points following injury has been shown to predict positive remodeling outcomes downstream, explant sections were immunolabeled with antibodies detecting macrophage polarization markers (B.N. Brown, et al., Macrophage phenotype as a predictor of constructive remodeling following the implantation of biologically derived surgical mesh materials, Acta biomaterialia 8(3) (2012) 978-87). F4/80 was used as a marker for overall macrophage presence within the implant zone at 7 days (FIG. 5A (A-D)). F4/80 immunolabeling showed an increased presence of F4/80+cells in FR-ECM repaired mice (FIG. 5B). This suggests that FR-ECM elicits a more robust macrophage response at acute time-points. iNOS immunolabeling was performed to detect presence of pro-inflammatory macrophages at 7 days post-implant (FIG. 5A (E-H)). There were no significant increases in iNOS immunolabeling at 7 days (FIG. 5C). Arginase-1 immunofluorescent labeling was performed to assess presence of anti-inflammatory macrophages at 7 days (FIG. 5A (I-L)). ROS ECM repair resulted in significantly increased arginase-1+ response over PAA and RNS ECM, suggesting an increased anti-inflammatory response (FIG. 5D). Heme oxygenase immunofluorescent staining was used to assess the presence of anti-oxidant macrophages at 7 days (FIG. 5A (M-P)). All FR-ECM resulted in significantly higher percentage of HO-1+cells at 7 days, indicating a robust anti-oxidant response over PAA ECM (FIG. 5E). The results from macrophage phenotyping indicate that free radical decellularization of ECM results in increased macrophage infiltration and increased anti-oxidant macrophage polarization. This response could be beneficial to a variety of regenerative and ischemic injury applications.

Evaluation of Chronic Remodeling Outcomes

Figure 6A:
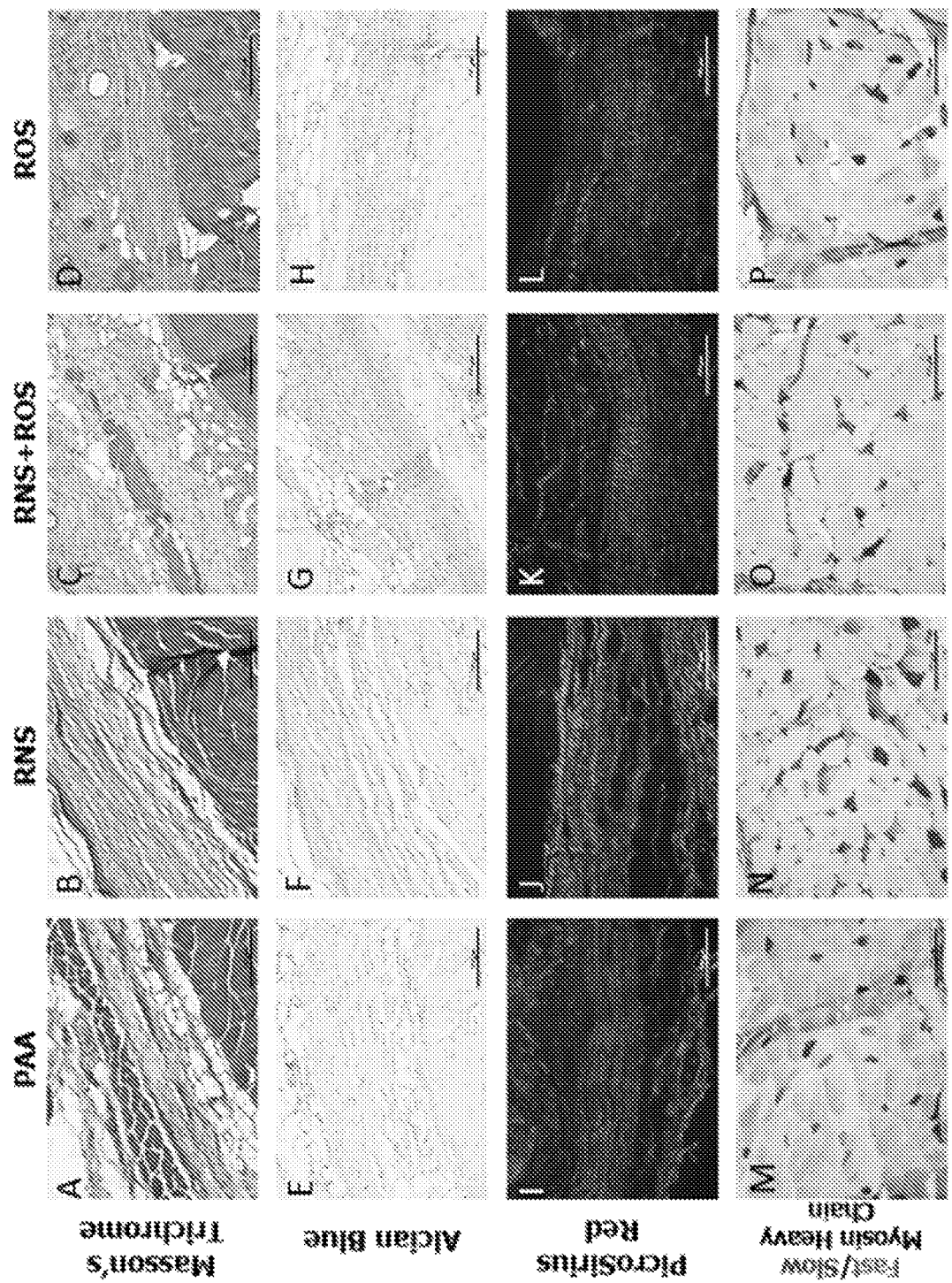
FIGS. 6A-6I: Histologic characterization of chronic 90 day ECM repair of abdominal wall defect. Histologic stains of 90 day explants for Masson's trichrome (FIG. 6A (A-D)), Alcian blue (FIG. 6A (E-H)), and polarized light microscopy of PicroSirius red (FIG. 6A (1-L)). Immunohistochemical staining for fast (pink) and slow (brown) myosin heavy chain (FIG. 6A (M-P)). Quantification of cellularity (FIG. 6B), collagen (FIG. 6C), glycosaminoglycan (FIG. 6D), and fast/slow myosin fiber ratio (FIG. 6E). Quantification of red (FIG. 6F), orange (FIG. 6G), yellow (FIG. 6H) and green (FIG. 6I) fiber types from polarized light-imaged PicroSirius Red tissue sections. Scale bars=100 μm. Results presented as mean ±S.D. (* represents $p<0.05$, $p<0.01$, * $p<0.001$, **** $p<0.0001$).
Figure 6B:
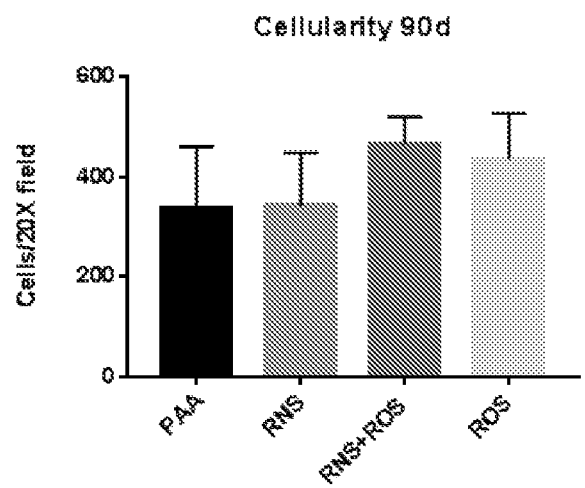
Figure 6C:
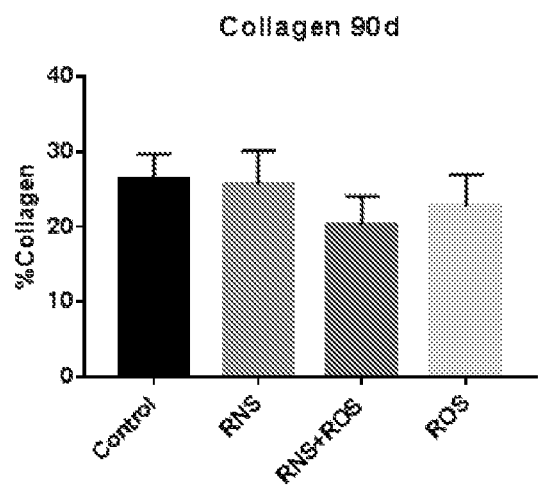
Figure 6D:
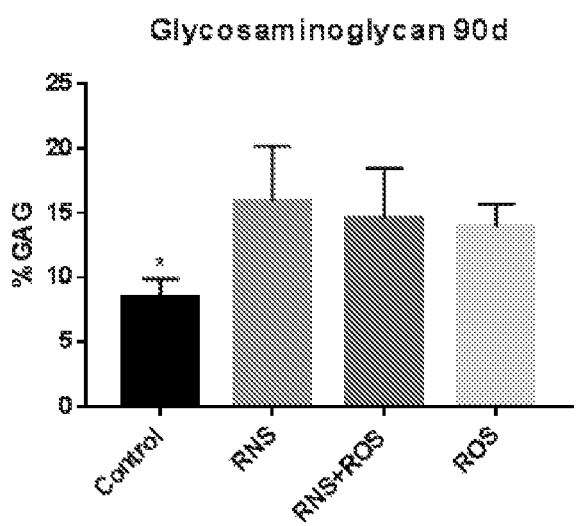
Figure 6E:
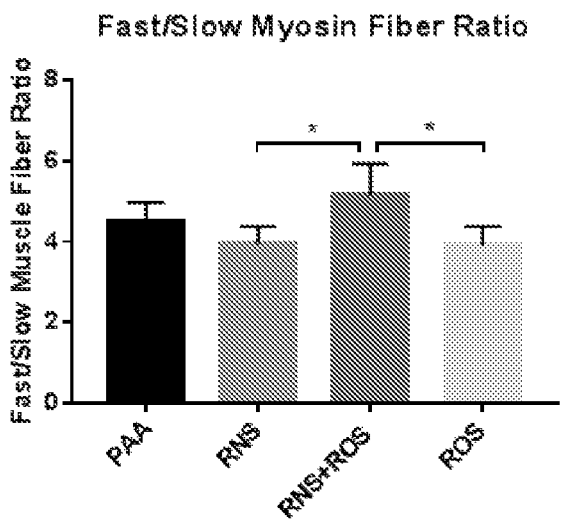
Figure 6F:
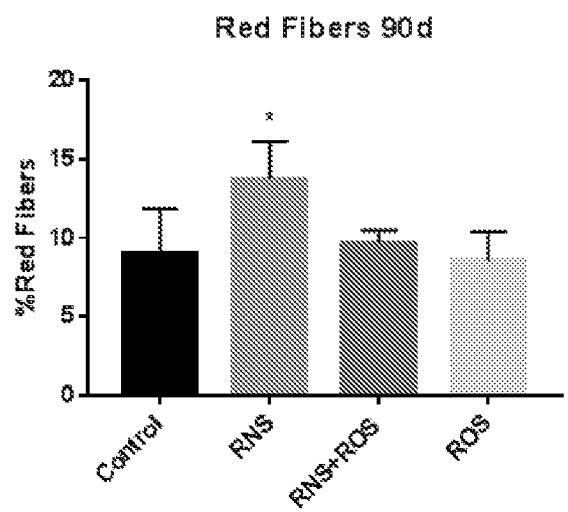
Figure 6G:
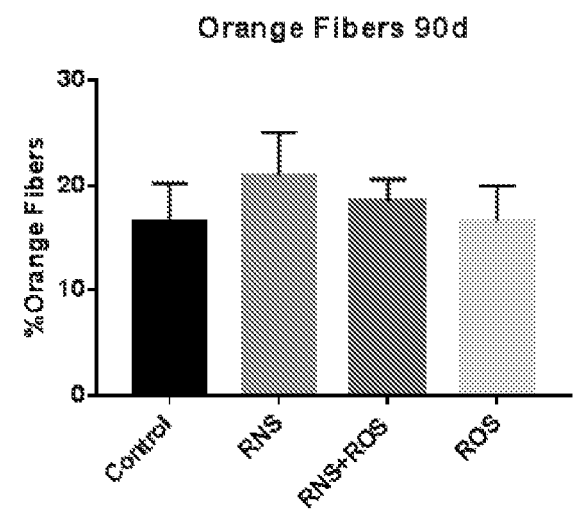
Figure 6H:
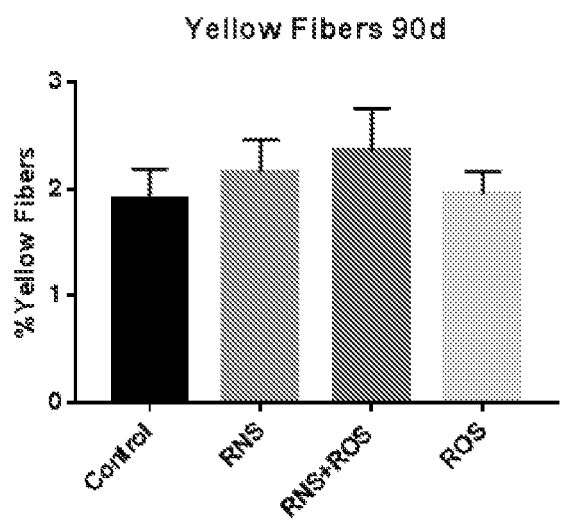
Figure 6I:
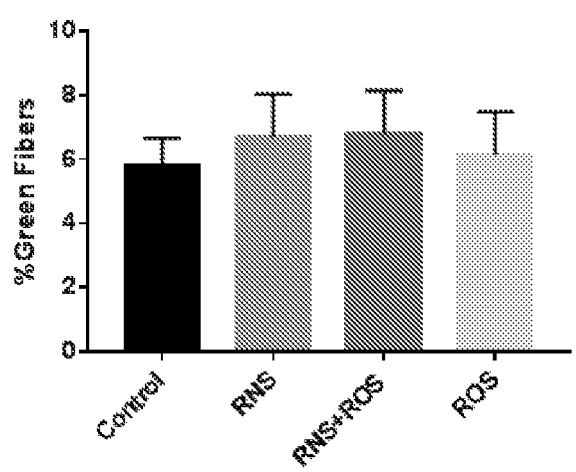

Explants from ECM repair of abdominal wall defects were taken 90 days post-implantation to assess the effect of FR decellularization upon constructive remodeling outcomes. There were no significant differences in cellularity at 90 days, suggesting there were no differences in ongoing inflammation (FIG. 6B). There were no differences in Masson's trichrome staining, which suggests that there was no significant differences in fibrotic outcomes (FIG. 6C). FR-ECM implantation resulted in a significant increase in Alcian blue staining at 90 days, indicative of increased glycosaminoglycan deposition (FIG. 6D). Glycosaminoglycans are important factors in wound healing, which assist with growth factor sequestration and activity, capillary growth and collagen formation. Picrosirius red staining imaged with circularly polarized light was used to assess collagen alignment (FIG. 6I-L). RNS ECM had increased levels of red fibers, indicating more highly aligned collagen fibrils than the other ECM types (FIG. 6F). There were no significant differences in any of the other groups of fiber alignment (FIGS. 6G-6I). In order to assess quality of muscle healing following regeneration, fast and slow muscle fibers were identified via immunohistochemistry (FIG. 6M-P). RNS and ROS ECM had significantly lower fast: slow muscle fiber ratio at 90 days compared to RNS+ROS ECM (FIG. 6T). This could be due to unresolved muscle healing as there is an increased presence of slow muscle fibers during acute muscle injury.

The present study sought to investigate the feasibility of decellularizing ECM biomaterials using radical inflammatory species, as well as the effect of these ECM on macrophage responses in vitro and within an in vivo model of abdominal wall repair. The results presented herein suggest that reactive nitrogen species, reactive oxygen species or the combination of the two are effective reagents for the decellularization of extracellular matrix biomaterials. These reagents also functionalized ECM biomaterials with natural nitroxidative and oxidative modifications similar to those produced during a normal inflammatory event. These modifications could be useful for tailoring ECM biomaterials to have an enhanced inflammatory response that could be beneficial in certain wound repair or disease treatment.

The following numbered clauses describe exemplary aspects or embodiments of the invention.

Clause 1. A method of preparing an extracellular matrix (ECM) product, comprising contacting tissue or an ECM material with a reactive oxygen species (ROS) or a reactive nitrogen species (RNS) to produce an ECM product having nitroxidative or oxidative modifications.

Clause 2. The method of clause 1, comprising contacting an ECM material with the ROS or RNS to produce the ECM product having nitroxidative or oxidative modifications.

Clause 3. The method of clause 1, comprising contacting tissue with the ROS or RNS to produce an ECM product, washing the ECM product, and drying the ECM product, e.g. by lyophilization.

Clause 4. The method of clause 1, comprising contacting tissue with the ROS or RNS to produce the ECM product having nitroxidative or oxidative modifications.

Clause 5. The method of any one of clauses 1-4, comprising contacting the tissue or ECM material with an ROS.

Clause 6. The method of clause 5, wherein the ROS is hydroxide (OH.), Superoxide ($O_2^-$), nitric oxide (NO.), thiyl (RS.), forming $RSO_2$. in the presence of oxygen and copper or iron ions), peroxyl (ROO.), lipid peroxyl (LOO.), peroxynitrite ($ONOO^-$), hypochloric acid (HOCl), singlet oxygen ($^1O_2$), ozone ($O_3$), or lipid peroxide (LOOH).

Clause 7. The method of any one of clauses 1-4, comprising contacting the tissue or ECM material with an RNS.

Clause 8. The method of clause 7, wherein the RNS is nitric oxide, peroxynitrite ($ONOO^-$), peroxynitrous acid (ONOOH), nitroxyl anion ($NO^-$), nitryl chloride ($NO_2Cl$), nitrosyl cation ($NO^+$), nitrogen dioxide ($NO_2$.), dinitrogen trioxide ($N_2O3$), or nitrous acid ($HNO_2$).

Clause 9. The method of clause 8, wherein the RNS is nitric oxide.

Clause 10. The method of clause 9, wherein the nitric oxide is bubbled into an aqueous solution containing the tissue or ECM material.

Clause 11. The method of clause 9, comprising producing nitric oxide by combining nitric acid and copper in an aqueous solution containing the tissue or ECM material.

Clause 12. The method of clause 9, comprising producing nitric oxide by reducing sodium nitrite or potassium nitrite in an aqueous solution containing the tissue or ECM material.

Clause 13. The method of any one of clauses 1-4, comprising contacting the tissue or ECM material with a Fenton's reagent, such as $H_2O_2$ or peracetic acid and a d-metal ion.

Clause 14. The method of clause 13, wherein the d-metal ion is $Fe^{2+}$, Cu(I), Mn(II), V(II), Co(II), Cr(II), Ru(II), Ni(II) or Ti(III).

Clause 15. The method of any one of clauses 1-14, further comprising digesting the ECM product with a proteinase to solubilize the ECM product.

Clause 16. The method of clause 15, wherein the ECM product is solubilized with an acid protease under acidic conditions.

Clause 17. The method of clause 16, further comprising neutralizing the acid protease-digested ECM product at a pH ranging from 6.8 to 7.8.

Clause 18. The method of any one of clauses 1-17, further comprising drying, for example lyophilizing, the ECM product or protease-digested ECM product.

Clause 19. The method of any one of clauses 1-17, further comprising combining the ECM product or protease-digested ECM product with a matrix or mesh comprising a synthetic polymer composition.

Clause 20. The method of clause 19, wherein the synthetic polymer composition is bioerodible.

Clause 21. The method of clause 20, wherein the synthetic polymer composition is a polyurethane, a polycarbonate, a polyacrylate or polymethacrylate, a polyacrylamide or polymethacrylamide, a polyester, a polyester-containing copolymer, a polyanhydride, a polyanhydride-containing copolymer, a polyorthoester, or a polyorthoester-containing copolymer.

Clause 22. An ECM product prepared by the method of any one of clauses 1-21.

Clause 23. The ECM product of clause 22, comprising at least a two-fold increase in protein carbonyl moieties, protein nitrotyrosine moieties, or protein nitrocysteine moieties as compared to the same tissue or ECM material not contacted with the ROS or RNS.

Clause 24. The ECM product of clause 22, comprising at least a five-fold increase in protein carbonyl moieties, protein nitrotyrosine moieties, or protein nitrocysteine moieties as compared to the same tissue or ECM material not contacted with the ROS or RNS.

Clause 25. The ECM product of clause 22, wherein the ECM product is produced by contacting the tissue or ECM material with an ROS, the ECM product comprising at least a two-fold increase in protein carbonyl moieties as compared to the same tissue or ECM material not contacted with the ROS.

Clause 26. The ECM product of clause 22, wherein the ECM product is produced by contacting the tissue or ECM material with an RNS, the ECM product comprising at least a two-fold increase in protein nitrotyrosine moieties or protein nitrocysteine moieties as compared to the same tissue or ECM material not contacted with the RNS.

Clause 27. The ECM product of clause 22, wherein the ECM product is produced by contacting the tissue or ECM material with an ROS, and the ECM product comprising at least a two-fold increase in oxidized lipid products as compared to the same tissue or ECM material not contacted with the ROS.

Clause 28. The ECM product of clause 22, wherein the ECM product is produced by contacting the tissue or ECM material with an RNS, and the ECM product comprising at least a two-fold increase in a nitrated lipid product as compared to the same tissue or ECM material not contacted with the RNS.

Clause 29. The ECM product of any one of clauses 22-28, further comprising matrix-bound vesicles prepared from tissue or an ECM material.

Clause 30. The ECM product of clause 29, wherein the matrix-bound vesicles are prepared from tissue or an ECM material that is contacted with an ROS or an RNS.

Clause 31. The ECM product of any one of clauses 22-30, further comprising a mesh or matrix of a synthetic polymer composition.

Clause 32. A method of treating a wound, injury, or defect in a patient, comprising administering to the patient at or about the site of the wound, injury, or defect, an amount of an ECM product prepared by the method of any one of clauses 1-21 effective to treat a wound or defect in a patient.

Clause 33. The method of clause 32, wherein the wound, injury, or defect is a chronic wound.

Clause 34. The method of clause 33, wherein the wound, injury, or defect is a diabetic foot ulcer.

Clause 35. The method of clause 32, wherein the ECM product is in the form of a mesh or sheet and the wound, injury, or defect is an abdominal wall wound, injury, or defect.

Clause 36. The method of clause 32, wherein the wound, injury, or defect is an ischemic injury, such as atherosclerosis, stroke, myocardial infarction and osteoarthritis.

Clause 37. The method of clause 32, wherein the wound, injury, or defect results from or is related to a degenerative disease, such as a neurodegenerative disease, including a neurodegenerative disease affected by oxidative stress, such as multiple sclerosis, Alzheimer's disease, or Parkinson's disease.

Clause 38. The method of clause 32, for tissue reconstruction, such as for vascular and nerve repair, hernia repair, breast reconstruction, pelvic organ reconstruction, reconstruction following cancer treatment, reconstruction following radiation treatment, repair of traumatic wounds, such as brain injury, spinal cord injury, or treatment of burns.

Clause 39. The method of clause 32, for cartilage repair, replacement, or regeneration.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:

1. A method of preparing an extracellular matrix (ECM) product, comprising directly contacting tissue or an ECM material with a composition, the composition comprising:
a reactive oxygen species (ROS) selected from hydroxyl radical (OH), Superoxide ($O_2^-$), nitric oxide (NO.), thiyl (RS.), forming $RSO_2$. in the presence of oxygen and copper or iron ions, peroxyl (ROO.), lipid peroxyl (LOO.), peroxynitrite (ONOO⁻), hypochloric acid (HOCl), singlet oxygen ($^1O_2$), ozone ($O_3$), and lipid peroxide (LOOH); and/or a reactive nitrogen species (RNS) selected from nitric oxide, peroxynitrite (ONOO⁻), peroxynitrous acid (ONOOH), nitroxyl anion (NO⁻), nitryl chloride ($NO_2Cl$), nitrosyl cation (NO⁺), nitrogen dioxide ($NO_2$.), dinitrogen trioxide ($N_2O_3$), or nitrous acid ($HNO_2$), thereby producing an ECM product having nitroxidative or oxidative modifications, and comprising at least a two-fold increase in protein carbonyl moieties, protein nitrotyrosine moieties, or protein nitrocysteine moieties as compared to the same tissue or ECM material not contacted with the ROS and/or RNS.

2. The method of claim 1, comprising directly contacting an ECM material with the ROS or RNS to produce the ECM product having nitroxidative or oxidative modifications.

3. The method of claim 1, comprising directly contacting tissue with the ROS or RNS to produce an ECM product, washing the ECM product, and drying the ECM product.

4. The method of claim 1, comprising directly contacting tissue with the ROS or RNS to produce the ECM product having nitroxidative or oxidative modifications.

5. The method of claim 1, comprising directly contacting the tissue or ECM material with hydroxyl radical (OH.), Superoxide ($O_2^-$), nitric oxide (NO.), thiyl (RS.), forming $RSO_2$. in the presence of oxygen and copper or iron ions, peroxyl (ROO.), lipid peroxyl (LOO.), peroxynitrite (ONOO⁻), hypochloric acid (HOCl), singlet oxygen ($^1O_2$), ozone ($O_3$), or lipid peroxide (LOOH).

6. The method of claim 1, comprising directly contacting the tissue or ECM material with nitric oxide, peroxynitrite (ONOO⁻), peroxynitrous acid (ONOOH), nitroxyl anion (NO⁻), nitryl chloride ($NO_2Cl$), nitrosyl cation (NO⁺), nitrogen dioxide ($NO_2$.), dinitrogen trioxide ($N_2O_3$), or nitrous acid ($HNO_2$).

7. The method of claim 6, comprising producing nitric oxide by combining nitric acid and copper in an aqueous solution containing the tissue or ECM material.

8. The method of claim 6, comprising producing nitric oxide by reducing sodium nitrite or potassium nitrite in an aqueous solution containing the tissue or ECM material.

9. The method of claim 1, comprising directly contacting the tissue or ECM material with a solution comprising an ROS formed from $H_2O_2$ or peracetic acid and $Fe^{2+}$, Cu(I), Mn(II), V(II), Co(II), Cr(II), Ru(II), Ni(II) or Ti(III).

10. The method of claim 1, further comprising digesting the ECM product with a proteinase to solubilize the ECM product.

11. The method of claim 10, wherein the ECM product is solubilized with an acid protease under acidic conditions, and optionally further comprising neutralizing the acid protease-digested ECM product at a pH ranging from 6.8 to 7.8.

12. The method of claim 1, further comprising drying the ECM product.

13. The method of claim 1, further comprising combining the ECM product with a matrix or mesh comprising a polyurethane, a polycarbonate, a polyacrylate or polymethacrylate, a polyacrylamide or polymethacrylamide, a polyester, a polyester-containing copolymer, a polyanhydride, a polyanhydride-containing copolymer, a polyorthoester, or a polyorthoester-containing copolymer.

* * * * *

UNITED STATES PATENT AND TRADEMARK OFFICE
CERTIFICATE OF CORRECTION

| | | |
|---|---|---|
| PATENT NO. | : 12,070,530 B2 | Page 1 of 1 |
| APPLICATION NO. | : 16/761371 | |
| DATED | : August 27, 2024 | |
| INVENTOR(S) | : Samuel LoPresti et al. | |

It is certified that error appears in the above-identified patent and that said Letters Patent is hereby corrected as shown below:

On the Title Page

Column 1, Line 9, item (86) after "application" insert -- is the United States national phase of International Application No. PCT/US2018/060051 filed November 9, 2018, and --

Column 1, Line 10, item (60) after "2017," insert -- each of --

In the Claims

Column 30, Line 65, Claim 1, delete "(OH)," and insert -- (OH·), --

Column 31, Line 11, Claim 1, delete "modifications," and insert -- modifications --

Signed and Sealed this
Third Day of December, 2024

*Katherine Kelly Vidal*

Katherine Kelly Vidal
*Director of the United States Patent and Trademark Office*